US011020012B2

(12) United States Patent
Sato et al.

(10) Patent No.: US 11,020,012 B2
(45) Date of Patent: Jun. 1, 2021

(54) FLOW RATE CONTROL APPARATUS AND BLOOD PRESSURE MONITOR

(71) Applicant: OMRON HEALTHCARE Co., Ltd., Kyoto (JP)

(72) Inventors: Hironori Sato, Kyoto (JP); Hiroyuki Kinoshita, Kyoto (JP); Toshihiko Ogura, Kyoto (JP); Yoshihiko Sano, Kyoto (JP); Takeshi Kubo, Kyoto (JP); Gaku Hasegawa, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 712 days.

(21) Appl. No.: 15/440,282

(22) Filed: Feb. 23, 2017

(65) Prior Publication Data
US 2017/0156603 A1  Jun. 8, 2017

Related U.S. Application Data

(63) Continuation of application No. PCT/JP2015/069492, filed on Jul. 7, 2015.

(30) Foreign Application Priority Data

Sep. 3, 2014  (JP) .............................. JP2014-179479

(51) Int. Cl.
*A61B 5/0235* (2006.01)
*A61B 5/022* (2006.01)
(Continued)

(52) U.S. Cl.
CPC ............ *A61B 5/0235* (2013.01); *A61B 5/022* (2013.01); *A61B 5/0225* (2013.01);
(Continued)

(58) Field of Classification Search
None
See application file for complete search history.

(56) References Cited

U.S. PATENT DOCUMENTS 4,522,371 A * 6/1985 Fox ..................... F16K 31/0651
                                                   251/129.21
4,951,224 A * 8/1990 Hokynar .............. G05D 7/0635
                                                       340/606
(Continued)

FOREIGN PATENT DOCUMENTS

EP    2644089 A1    10/2013
JP    H6-245911 A    9/1994
(Continued)

OTHER PUBLICATIONS

"Correlation". Merriam-Webster.com. 2019. Retrieved Oct. 22, 2019, from www.merriam-webster.com/dictionary/correlation (Year: 2019).*
(Continued)

*Primary Examiner* — Matthew Kremer
*Assistant Examiner* — Samuel C Kim
(74) *Attorney, Agent, or Firm* — Osha Bergman Watanabe & Burton LLP

(57) ABSTRACT

A flow rate control apparatus includes a flow rate detection unit that detects the flow rate of a fluid flowing through a solenoid valve, a correlation storage unit that stores a correlation between a flow start point voltage at which the fluid starts to flow through a sample solenoid valve, which has substantially the same characteristic as the solenoid valve, and a limit voltage at which the sample solenoid valve is fully open, and a control unit that, when starting control of the flow rate of the fluid, changes the driving voltage of the solenoid valve, obtains the driving voltage at a time when the start of flowing of the fluid is detected as the flow start point voltage, and uses the correlation for the sample (Continued)

solenoid valve to set the driving voltage of the solenoid valve within a range between the flow start point voltage and the limit voltage.

15 Claims, 16 Drawing Sheets

(51) Int. Cl.
    *A61B 5/0225*     (2006.01)
    *F16K 31/06*     (2006.01)
    *G05D 7/06*     (2006.01)

(52) U.S. Cl.
    CPC ...... *A61B 5/02233* (2013.01); *F16K 31/0658* (2013.01); *F16K 31/0675* (2013.01); *G05D 7/06* (2013.01); *G05D 7/0635* (2013.01)

(56) References Cited

U.S. PATENT DOCUMENTS

| | | | | |
|---|---|---|---|---|
| 6,072,525 | A * | 6/2000 | Kaneda | G01S 3/7864 |
| | | | | 348/169 |
| 6,602,200 | B1 * | 8/2003 | Kubo | A61B 5/0225 |
| | | | | 600/485 |
| 2004/0069348 | A1 * | 4/2004 | Jacobs | G05D 7/0635 |
| | | | | 137/487.5 |
| 2013/0037112 | A1 * | 2/2013 | Smirnov | G05D 7/0635 |
| | | | | 137/1 |
| 2014/0116538 | A1 * | 5/2014 | Tanaka | G05D 7/0635 |
| | | | | 137/486 |

FOREIGN PATENT DOCUMENTS

| | | |
|---|---|---|
| JP | 2000-9249 A | 1/2000 |
| JP | 2012-65939 A | 4/2012 |
| JP | 2014-55607 A | 3/2014 |

OTHER PUBLICATIONS

Linear. 2020. In Merriam-Webster.com. Retrieved May 9, 2020, from www.merriam-webster.com (Year: 2020).*

International Search Report issued in corresponding Application No. PCT/JP2015/069492, dated Oct. 6, 2015 (5 pages).

Written Opinion issued in corresponding Application No. PCT/JP2015/069492, dated Oct. 6, 2015 (3 pages).

* cited by examiner

FLOW RATE CONTROL APPARATUS AND BLOOD PRESSURE MONITOR

TECHNICAL FIELD

The present invention relates to a flow rate control apparatus, and more specifically relates to a flow rate control apparatus that controls a flow rate of a fluid with a solenoid valve.

Also, the present invention relates to a blood pressure monitor including such a flow rate control apparatus.

BACKGROUND ART

Conventionally, as disclosed in Patent Literature 1 (JP H6-245911A) for example, there have been known to be blood pressure monitors that control a flow rate of air serving as a fluid using a solenoid valve, and thereby adjust the pressure of a cuff (or more accurately, the pressure of a fluid bladder in the cuff) for restricting blood flow at a measurement site.

CITATION LIST

Patent Literature

Patent Literature 1: JP H6-245911A

SUMMARY OF INVENTION

It is often the case that this type of blood pressure monitor uses a normally-open type (a type in which the flow path of the valve is fully-open at a non-conducting time) of solenoid valve for flow rate control, a driving voltage is applied to a solenoid of the solenoid valve at an operation time, and the valve body is moved by the electromagnetic force of the solenoid so as to adjust the cross-sectional area of the flow path. Because the solenoid valve is in the fully-open state at a non-conducting time, the cuff is not inflated. The purpose of this is to achieve safety for the measurement subject when the power is off (electricity is stopped), such as a time when an accident occurs.

In general, the flow rate to driving voltage characteristic of such a solenoid valve is such that if the effective driving voltage (and accordingly, the flowing current) is sufficiently high, the solenoid valve will close completely, and the flow rate will reach zero. When the driving voltage decreases to a certain value (this is called the "flow start point voltage"), the solenoid valve opens and the fluid starts to flow. If the driving voltage decreases further, the flow rate gradually increases, and when the driving voltage is below the limit (this is called the "limit voltage"), the solenoid valve is completely open and the flow rate increases dramatically (i.e., the flow rate is uncontrollable). Accordingly, the driving voltage of the solenoid valve during operation needs to be set within a range (this is called the "effective setting range" as needed) between the flow start point voltage and the limit voltage.

Here, when the blood pressure monitor performs measurement, it is often the case that the cuff pressure is temporarily increased to be greater than the systolic blood pressure of the measurement subject and then the pulse wave at the measurement site is observed in a deflation process thereafter. In this case, at the deflation start time, it is desirable that the discharge flow rate is increased and deflation is performed rapidly by setting the driving voltage of the solenoid valve within the effective setting range in the vicinity of the limit voltage.

However, the limit voltage of the solenoid valve sometimes changes due to factors such as the cuff pressure (pressure on the upstream side of the solenoid valve), the ambient temperature, and variation between individual products. For this reason, when the driving voltage of the solenoid valve is to be set within the effective setting range in the vicinity of the limit voltage, there is a possibility that the driving voltage will fall below the limit voltage of the solenoid valve. If the driving voltage of the solenoid valve temporarily falls below the limit voltage, the flow rate will dramatically increase, the cuff pressure will drop suddenly, and the pressure range for observing the pulse wave cannot be sufficiently secured. In particular, these effects are more severe in low-cost solenoid valves, which tend to have narrow effective setting ranges.

In view of this, an advantage of one or more embodiments of the present invention is to provide a flow rate control apparatus that controls the flow rate of a fluid by opening and closing a solenoid valve using a driving voltage, and that can set the driving voltage of the solenoid valve accurately within the effective setting range.

Also, an advantage of one or more embodiments of the present invention is to provide a blood pressure monitor that includes such a flow rate control apparatus and that can shorten the amount of time needed for blood pressure measurement.

Embodiments of the present invention have been created based on the finding of the inventor, the finding being that regarding the driving voltage for opening and closing the solenoid valve, there is a correlation between the flow start point voltage at which a fluid starts to flow through the solenoid valve and the limit voltage at which the solenoid valve is fully open.

Accordingly, a flow rate control apparatus according to one or more embodiments of the present invention is a flow rate control apparatus for controlling a flow rate of a fluid by opening and closing a solenoid valve using a driving voltage, including: a flow rate detection unit configured to detect the flow rate of a fluid flowing through the solenoid valve; a correlation storage unit storing, for a sample solenoid valve having substantially the same characteristic as the solenoid valve, a correlation between a flow start point voltage at which the fluid starts to flow through the sample solenoid valve and a limit voltage at which the sample solenoid valve is fully open; and a control unit configured to, when starting control of the flow rate of the fluid, change the driving voltage of the solenoid valve, obtain the driving voltage at a time when the flow rate detection unit detects the start of flowing of the fluid as the flow start point voltage, use the correlation for the sample solenoid valve based on the flow start point voltage of the solenoid valve to obtain the limit voltage at which the solenoid valve is filly open through conversion, and thereafter set the driving voltage of the solenoid valve within a range between the flow start point voltage and the limit voltage.

Here, a "solenoid valve" may be of either a normally-open type or a normally-closed type.

Also, the "sample solenoid valve having substantially the same characteristic" as the solenoid valve means a solenoid valve having substantially the same flow rate to driving voltage characteristic as the solenoid valve that controls the flow rate of the fluid. Being "substantially the same" means that differences in the individual characteristics due to manufacturing variations are allowed. For example, the "sample solenoid valve" may be another individual member having the same model number as the solenoid valve that controls the flow rate of the fluid, or it may be the solenoid valve itself. Also, there may be multiple "sample solenoid valves".

Regarding the "flow start point voltage" and the "limit voltage", depending on the type of the solenoid valve, there are cases where the flow start point voltage is higher than the limit voltage, and cases where the flow start point voltage is lower than the limit voltage.

With the flow rate control apparatus according to one or more embodiments of the present invention, regarding the sample solenoid valve having substantially the same characteristic as the solenoid valve to be driven, the correlation storage unit stores the correlation between the flow start point voltage at which the fluid flows through the sample solenoid valve and the limit voltage at which the sample solenoid valve is fully open. When starting the control of the flow rate of the fluid, the control unit changes the driving voltage of the solenoid valve and obtains the driving voltage at the time when the flow rate detection unit detects the start of flowing of the fluid as the flow start point voltage (note that the changing of the driving voltage at that time is changed in the vicinity of the flow start point voltage, or in other words, in a region that is sufficiently separated from the limit voltage). Next, according to the flow start point voltage of the solenoid valve, the control unit obtains the limit voltage at which the solenoid valve is fully open through conversion, based on the correlation for the sample solenoid valve. Thereafter, the control unit controls the flow rate of the fluid by setting the driving voltage of the solenoid valve within a range (effective setting range) between the flow start point voltage and the limit voltage and opening and closing the solenoid valve according to the driving voltage.

Thus, with the flow rate control apparatus according to one or more embodiments of the present invention, the limit voltage at which the solenoid valve is fully open is obtained through conversion using the correlation for the sample solenoid valve, and therefore the driving voltage of the solenoid valve can be set accurately within the effective setting range.

With the flow rate control apparatus according to an embodiment, the correlation for the sample solenoid valve stored by the correlation storage unit includes a correlation at a time when a plurality of varied pressures of the fluid are set.

Here, the "pressure" of the fluid means the differential pressure between the upstream side and the downstream side, which is applied to the sample solenoid valve.

When the pressure of the fluid changes, the force of the fluid pressing the valve body of the solenoid valve against the electromagnetic force of the solenoid included in the solenoid valve (or the sample solenoid valve) changes. For this reason, even if the effective driving voltage is the same, the flow rate of the fluid passing through the solenoid valve changes. There is a possibility that the correlation between the flow start point voltage and the limit voltage will change accompanying this. In view of this, with the flow rate control apparatus according to the embodiment, the correlation for the sample solenoid valve stored in the correlation storage unit includes a correlation at a time when a plurality of varied pressures of the fluid are set. Accordingly, the limit voltage of the solenoid valve is obtained with consideration given to the pressure of the fluid. Accordingly, the driving voltage of the solenoid valve can be set with further accuracy within the effective setting range.

With the flow rate control apparatus according to an embodiment, a pressure sensor configured to detect the pressure of the fluid is included, in which the control unit detects the pressure of the fluid using the pressure sensor at a control start time, when the pressure of the fluid at the control start time takes a value other than those of the plurality of pressures that give the correlation stored in the correlation storage unit, the control unit uses interpolation or extrapolation based on the correlation corresponding to the plurality of pressures to obtain a correlation between the flow start point voltage and the limit voltage corresponding to the pressure of the fluid at the control start time, and the control unit uses the obtained correlation when obtaining the limit voltage through conversion based on the flow start point voltage of the solenoid valve.

With the flow rate control apparatus according to the embodiment, the control unit detects the pressure of the fluid using the pressure sensor at a control start time. When the pressure of the fluid at the control start time takes a value other than that of a plurality of pressures that give the correlation stored in the correlation storage unit, the control unit uses interpolation or extrapolation based on the correlation corresponding to the plurality of pressures to obtain the correlation between the flow start point voltage and the limit voltage corresponding to the pressure of the fluid at the control start time. Then, the obtained correlation is used when the limit voltage is obtained through conversion based on the flow start point voltage of the solenoid valve. Accordingly, even when the pressure of the fluid at the control start time takes a value other than that of the multiple pressures that give the correlation stored in the correlation storage unit, the driving voltage of the solenoid valve can be set accurately within the effective setting range.

With the flow rate control apparatus according to an embodiment, the control unit detects the current pressure of the fluid using the pressure sensor in the control period, and when the current pressure of the fluid changes from the pressure at the control start time, based on the correlation corresponding to the plurality of pressures, the control unit obtains the current flow start point voltage and limit voltage for the solenoid valve through conversion.

With the flow rate control apparatus according to the embodiment, the control unit detects the current pressure of the fluid using the pressure sensor. When the current pressure of the fluid changes from the pressure at the control start time, based on the correlation corresponding to the plurality of pressures, the control unit obtains the current flow start point voltage and limit voltage for the solenoid valve through conversion. Accordingly, even in the case where the pressure of the fluid changes in the control period, the driving voltage of the solenoid valve can be set accurately in real time within the effective setting range.

With the flow rate control apparatus according to an embodiment, the correlation for the sample solenoid valve includes a relationship at a time when a plurality of varied ambient temperatures are set.

Here, "ambient temperature" means the temperature of the environment surrounding the sample solenoid valve (or the solenoid valve).

When the ambient temperature changes, the electrical resistance of the solenoid included in the solenoid valve (or sample solenoid valve) changes. For this reason, even if the effective driving voltage is the same, the electrifying current for the solenoid valve changes, and the degree of opening of the solenoid valve changes. There is a possibility that the correlation between the flow start point voltage and the limit voltage will change accompanying this. In view of this, with the flow rate control apparatus according to the embodiment, the correlation for the sample solenoid valve includes a relationship at a time when a plurality of varied ambient temperatures are set. Accordingly, the limit voltage of the solenoid valve is obtained by adding the ambient temperature. Accordingly, the driving voltage of the solenoid valve can be set with further accuracy within the effective setting range.

With the flow rate control apparatus according to an embodiment, a temperature sensor configured to detect the ambient temperature of the solenoid valve is included, in which the control unit detects the current ambient temperature of the solenoid valve using the temperature sensor in the control period, and when the current ambient temperature of the solenoid valve changes from the ambient temperature at the control start time, based on the correlation corresponding to the plurality of ambient temperatures, the control unit obtains the current flow start point voltage and limit voltage for the solenoid valve through conversion.

With the flow rate control apparatus of the embodiment, the control unit detects the current ambient temperature of the solenoid valve using the temperature sensor in the control period. When the current ambient temperature of the solenoid valve changes from the ambient temperature at the control start time, based on the correlation corresponding to the plurality of ambient temperatures, the control unit obtains the current flow start point voltage and limit voltage for the solenoid valve through conversion. Accordingly, even in the case where the ambient temperature of the solenoid valve changes in the control period, the driving voltage of the solenoid valve can be set accurately in real time within the effective setting range.

A blood pressure monitor according to one or more embodiments of the present invention includes: a cuff for compressing a measurement site; a solenoid valve for adjusting a pressure of the cuff; and the flow rate control apparatus.

With the blood pressure monitor according to one or more embodiments of the present invention, at a deflation start time that occurs after the cuff pressure has been temporarily increased to be higher than the systolic blood pressure of the measurement subject, the driving voltage of the solenoid valve can be set accurately within the effective setting range, in the vicinity of the limit voltage. Accordingly, the pressure can be reduced quickly by increasing the flow rate for discharging air at the deflation start time. As a result, the amount of time needed for blood pressure measurement can be shortened. Also, since the driving voltage of the solenoid valve does not fall below the limit voltage, it is possible to avoid a situation in which the cuff pressure suddenly drops during blood pressure measurement, causing a measurement error. Also, it is easier to use a low-cost solenoid valve that tends to have a smaller effective setting range.

In particular, if the correlation for the sample solenoid valve includes a relationship at a time when a plurality of varied ambient temperatures are set, the limit voltage of the solenoid valve obtained through conversion by the control unit is obtained with consideration given to the ambient temperature. Moreover, it is often the case that the blood pressure measurement is performed in a relatively short period (typically about one minute), such that there is no need to consider a change in the ambient temperature T. In this case, even if a temperature sensor is not included, the driving voltage of the solenoid valve can be set accurately within the effective setting range.

ADVANTAGEOUS EFFECTS OF INVENTION

As is clear from the foregoing description, with the flow rate control apparatus according to one or more embodiments of the present invention, a driving voltage of a solenoid valve can be set accurately within an effective setting range.

Also, with the blood pressure monitor according to one or more embodiments of the present invention, an amount of time needed for blood pressure measurement can be shortened. Also, a situation can be avoided in which the cuff pressure suddenly drops during blood pressure measurement, causing a measurement error.

DESCRIPTION OF EMBODIMENTS

Hereinafter, an embodiment of the invention will be described in detail with reference to the drawings.

Figure 3:
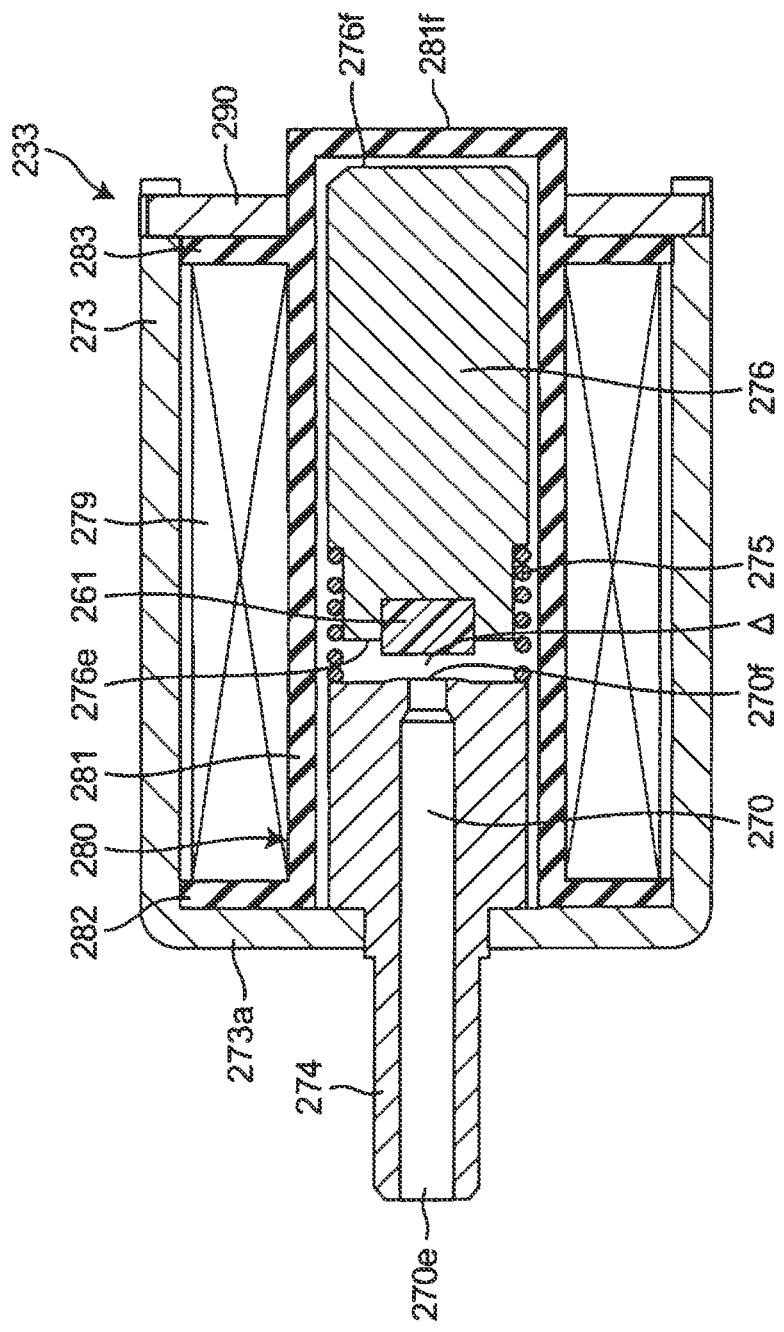
FIG. 3 is a diagram showing a structure of the solenoid valve.

FIG. 3 illustrates an example of a structure of a solenoid valve 233 that is to be controlled by a flow rate control apparatus according to an embodiment of the invention. The solenoid valve 233 is of a normally-open type, such as that mounted in "upper-arm blood pressure monitor HEM-7320F" manufactured by Omron Healthcare Corporation, for example.

The solenoid valve 233 includes a U-shaped yoke 273, an approximately cylindrical core 274 fixed to a wall 273a in the center of the yoke 273, a coil spring 275 serving as a biasing portion, an approximately rod-shaped plunger (movable iron core) 276, a bobbin 280 composed of a non-magnetic plastic material accommodated in the yoke 273, and an approximately rectangular plate-like yoke cover 290 for sealing the open end of the yoke 273. The yoke 273, the core 274, the plunger 276, and the yoke cover 290 are composed of a magnetic material so as to constitute a magnetic circuit during operation.

The bobbin 280 integrally includes a cylindrical portion 281 around which a solenoid coil 279 is wound, and a pair of end plates 282 and 283. The pair of end plates 282 and 283 are interposed between the wall in the center of the yoke 273 and the yoke cover 290 and are fixed to the yoke 273.

The core 274 penetrates through the wall 273a in the center of the yoke 273 and extends into the cylindrical portion 281 of the bobbin 280. A flow-through hole 270 for allowing a fluid to flow from an outer end 270e to an inner end 270f is formed inside of the core 274 so as to penetrate in the axis direction.

The plunger (movable iron core) 276 is accommodated in the cylindrical portion 281 of the bobbin 280 so as to be able to slide in the axis direction. A valve body 261 composed of an elastic member such as rubber is attached to one end (end portion on the side of the core 274 opposing the flow-through hole 270) 276e of the plunger 276.

The coil spring 275 is compressed between the core 274 and the plunger 276 so as to bias the plunger 276 in the direction of moving away from the core 274.

As shown in FIG. 3, at a non-operation time during which the solenoid coil 279 is in a non-conducting state, the valve body 261 provided on the one end 276e of the plunger 276 is separated from the inner end (end portion on the side opposing the valve body 261) 270f of the core 274 by the biasing force applied by the coil spring 275. Thus, a gap Δ between the inner end 270f of the core 274 and the valve body 261 is in a fully-open state. Also, the other end 276f of the plunger 276 protrudes outward from the yoke cover 290, and comes into contact with, and is engaged with the end portion 281f of the cylindrical portion 281 of the bobbin 280. A fluid is supplied from an upstream-side pressure source (not shown) to the outer end 270e of the core 274, and flows through the flow-through hole 270 and the above-described gap Δ to the cylindrical portion 281 (includes a fluid flow outlet (not shown) that is open to the outside environment) of the bobbin 280 on the downstream side.

Figure 4:
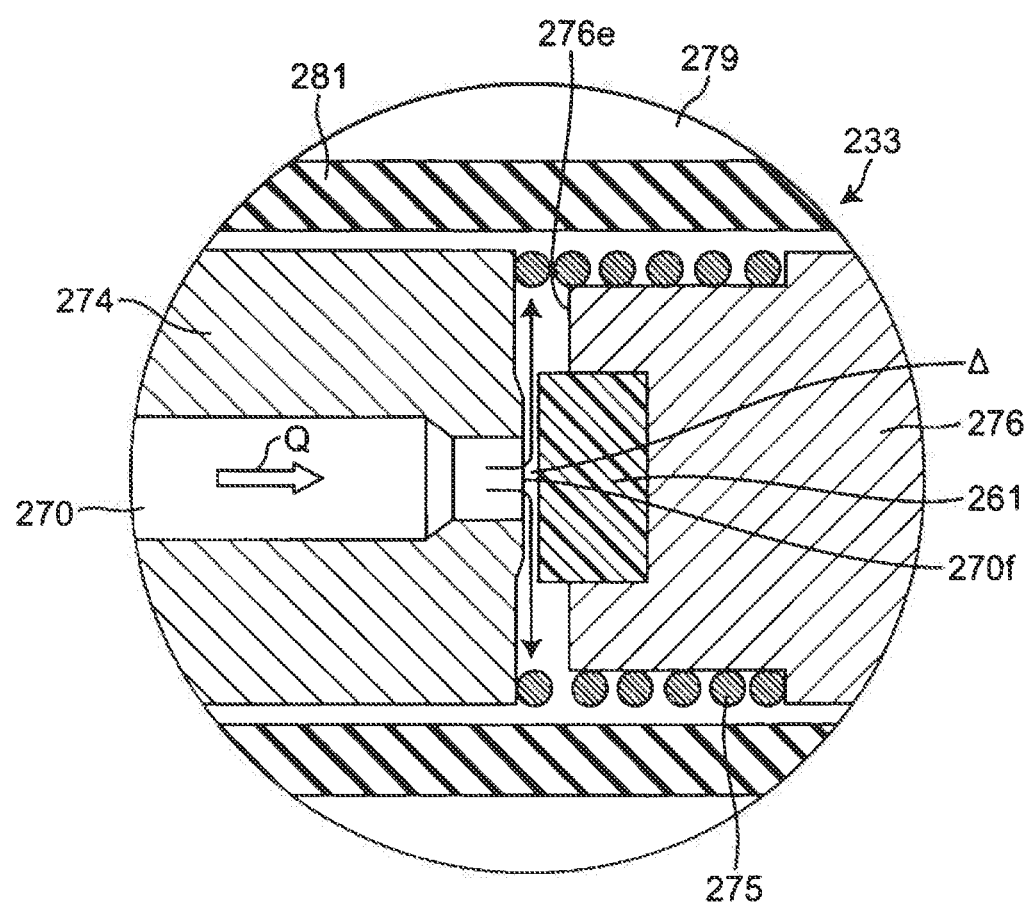
FIG. 4 is a diagram showing a state of the vicinity of a valve body when the solenoid valve operates.

As shown in FIG. 4, at an operation time during which the solenoid coil 279 is in the conductive state, the valve body 261 is moved together with the plunger 276 in the bobbin 280 against the biasing force applied by the coil spring 275 due to a In magnetic force generated by the solenoid coil 279. Accordingly, a state is entered in which the gap Δ between the inner end 270f of the core 274 and the valve body 261 is made narrow, and a flow rate Q of a fluid that flows through the flowthrough hole 270 is adjusted.

Figure 2A:
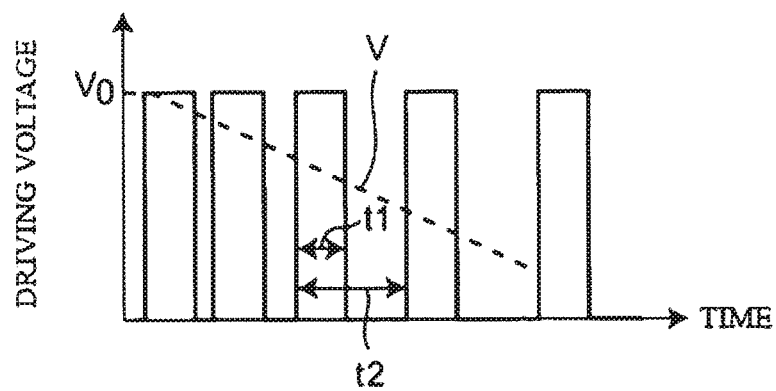
FIG. 2A is a diagram showing a waveform of a driving voltage applied to a solenoid valve by the flow rate control apparatus.
Figure 2B:
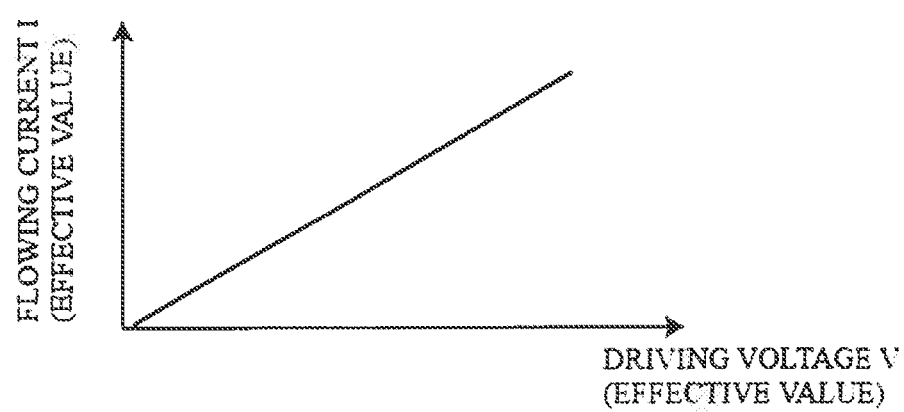
FIG. 2B is a diagram showing a relationship between a driving voltage (effective value) and flowing current (effective value) for the solenoid valve.

A driving voltage (peak value $V_0$) having a rectangular pulse wave shown in FIG. 2A, for example, is applied to the solenoid coil 279. A duty ratio (t1/t2) of the pulse wave is changed using PWM (pulse width modulation), whereby varied effective values V of the driving voltage are set. As shown in FIG. 2B, an effective value I of a flowing current in the solenoid coil 279 is proportional to the effective value V of the driving voltage. Hereinafter, the effective value of the driving voltage will be referred to simply as the driving voltage V. Also, the effective value of the flowing current will be referred to simply as the flowing current I.

Figure 5:
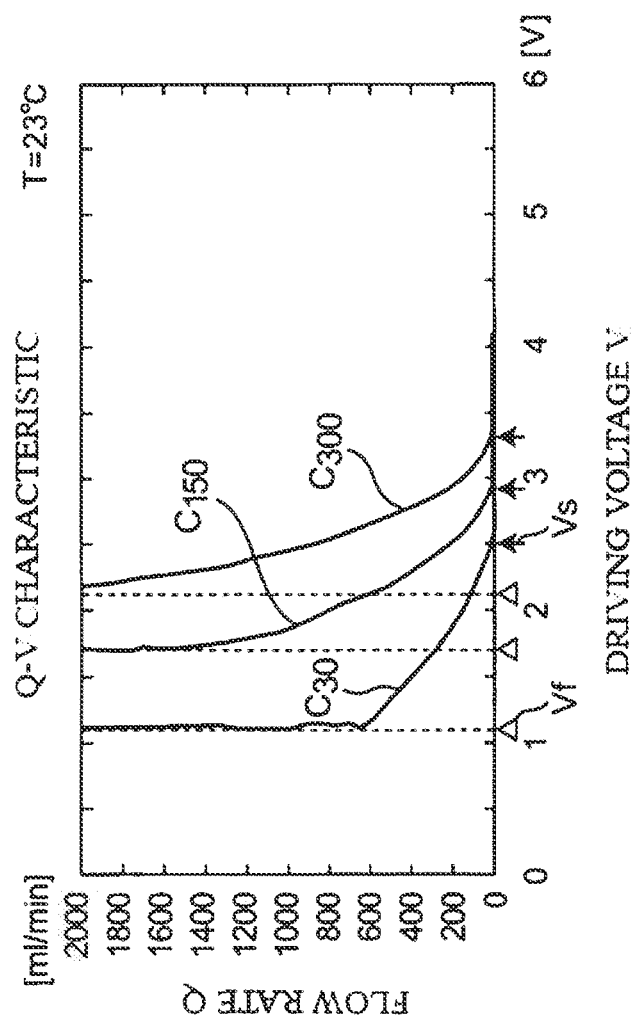
FIG. 5 is a diagram showing a flow rate to driving voltage characteristic (Q-V characteristic) at a ambient temperature T of 23° C. of the solenoid valve.
Figure 6:
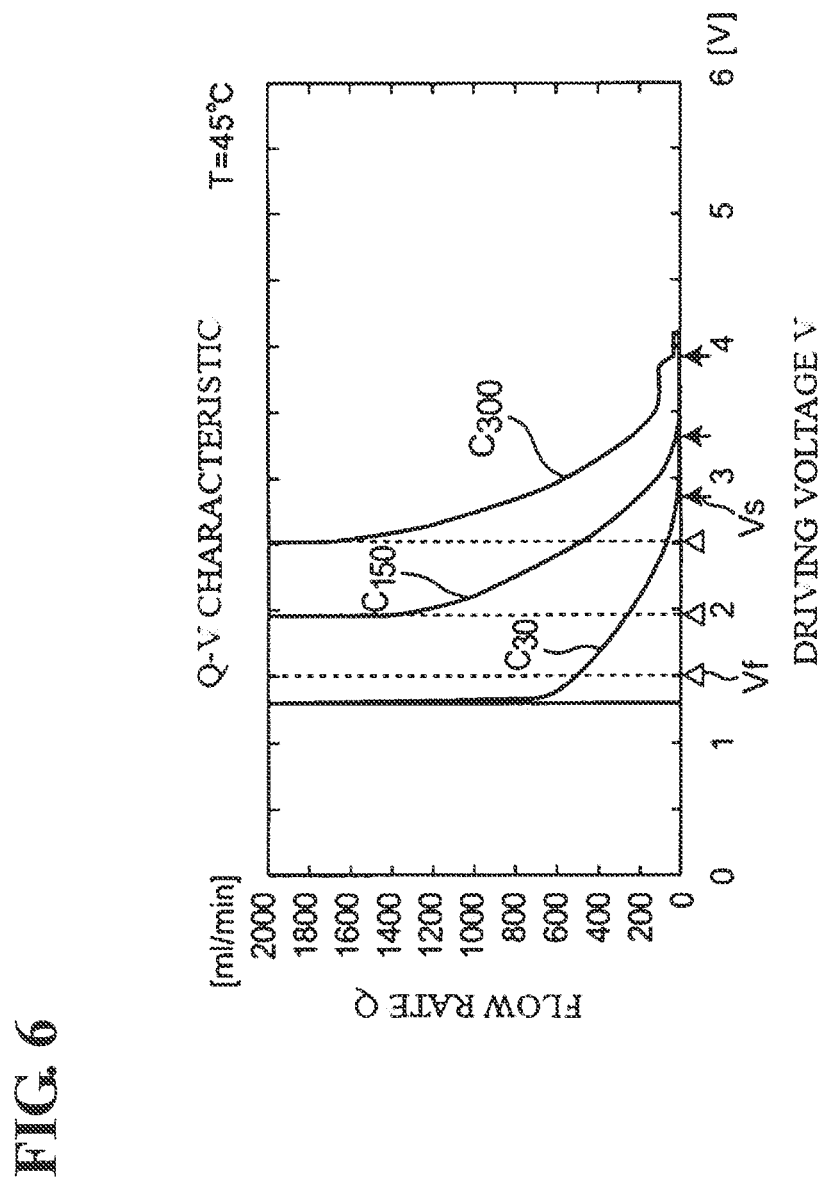
FIG. 6 is a diagram showing a Q-V characteristic at a ambient temperature T of 45° C. of the solenoid valve.
Figure 7:
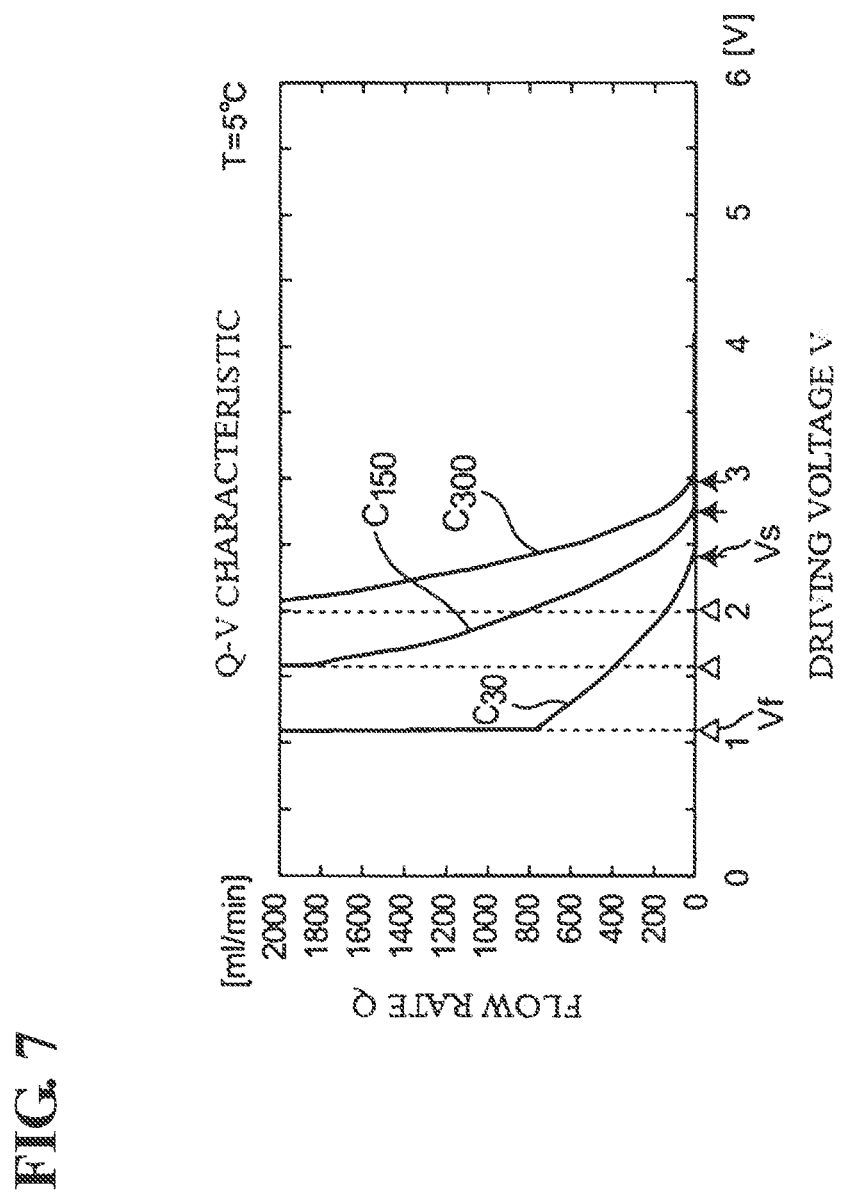
FIG. 7 is a diagram showing a Q-V characteristic at a ambient temperature T of 5° C. of the solenoid valve.

Regarding the air serving as the fluid, the solenoid valve 233 exhibits the flow rate to driving voltage characteristics (Q-V characteristics) shown in FIGS. 5 to 7 (the driving voltage V is plotted on the horizontal axis and the flow rate Q is plotted on the vertical axis). Also, the pressure of the air serving as the fluid supplied to the solenoid valve 233 (supplied to the outer end 270e of the flow-through hole 270 of the solenoid valve 233) from the upstream side is set variably as a parameter to 30 mmHg, 150 mmHg, and 300 mmHg (meaning the differential pressure with respect to the downstream-side atmospheric pressure; the same follows below). Note that the target that is to be subjected to flow rate control is not limited to being air, and therefore will be referred to as "fluid" as appropriate hereinafter.

As shown in FIG. 5, at an ambient temperature T of 23° C. (room temperature), the Q-V characteristic is shifted further upward and to the right as the pressure P on the upstream side of the solenoid valve increases from 30 mmHg to 150 mmHg and 300 mmHg, as indicated by the curves $C_{30}$, $C_{150}$, and $C_{300}$. The reason for this is that if the pressure P on the upstream side (left side) is higher in FIG. 4, for example, the force of the fluid pushing the valve body 261 increases against the electromagnetic force of the solenoid coil 279. For this reason, if the upstream-side pressure P increases, the flow rate Q of the fluid passing through the solenoid valve 233 increases even if the effective driving voltage V is the same. In other words, in order to maintain the same flow rate Q when the pressure P on the upstream side (left side) increases, the flowing current I flowing in the solenoid coil 279 (and accordingly the magnetic force) needs to be increased such that the valve body 261 and the plunger 276 are pressed to the upstream side with more force. In this example, as the pressure P on the upstream side increases from 30 mmHg to 150 mmHg and 300 mmHg, the flow start point voltage Vs at which the fluid starts to flow increases to about 2.5 V, 2.9 V, and 3.3 V (each being denoted by the sign ↑) in sequence, and the limit voltage Vf at which the solenoid valve 233 is completely open increases to about 1.1 V, 1.7 V, and 2.1 V (each being denoted by the sign Δ) in sequence.

As shown in FIG. 6, when the ambient temperature T is 45° C. (high temperature), the Q-V characteristic is shifted to the right side overall, relative to when the ambient temperature T is 23° C. (room temperature) in FIG. 5, The reason for this is that when the ambient temperature T increases, the electrical resistance of the solenoid coil 279 increases, and therefore the driving voltage V needs to be increased in order to maintain the same flowing current I. In this example, when the upstream-side pressures P are 30 mmHg, 150 mmHg, and 300 mmHg, the flow start point voltages Vs are about 2.8 V, 3.4 V, and 3.9 V (each being denoted by the sign ↑) and the limit voltages Vf are about 1.3 V, 1.9 V, and 2.5 V (each being denoted by the sign Δ) respectively.

Conversely, as shown in FIG. 7, when the ambient temperature T is 5° C. (low temperature), the Q-V characteristic is shifted to the left side overall, relative to when the ambient temperature T is 23° C. (room temperature) in FIG. 5. The reason for this is that if the ambient temperature T decreases, the electrical resistance of the solenoid coil 279 decreases, and therefore the driving voltage V needs to be reduced in order to maintain the same flowing current I. In this example, when the upstream-side pressures P are 30 mmHg, 150 mmHg, and 300 mmHg, the flow start point voltages Vs are about 2.4 V, 2.8 V, and 3.0 V (each being denoted by the sign ↑) and the limit voltages Vf are about 1.1 V, 1.6 V, and 2.0 V (each being denoted by the sign Δ) respectively.

As can be understood from FIGS. 5 to 7, when the upstream-side pressure P of the solenoid valve 233 or the ambient temperature T changes, the flow start point voltage Vs and the limit voltage Vf also change. Here, the inventor of embodiments of the present invention found that the same correlation between the flow start point voltage Vs and the limit voltage Vf is present in the solenoid valve 233 and solenoid valves (these will be referred to as "sample solenoid valves") having substantially the same Q-V characteristic thereas.

Figure 8:
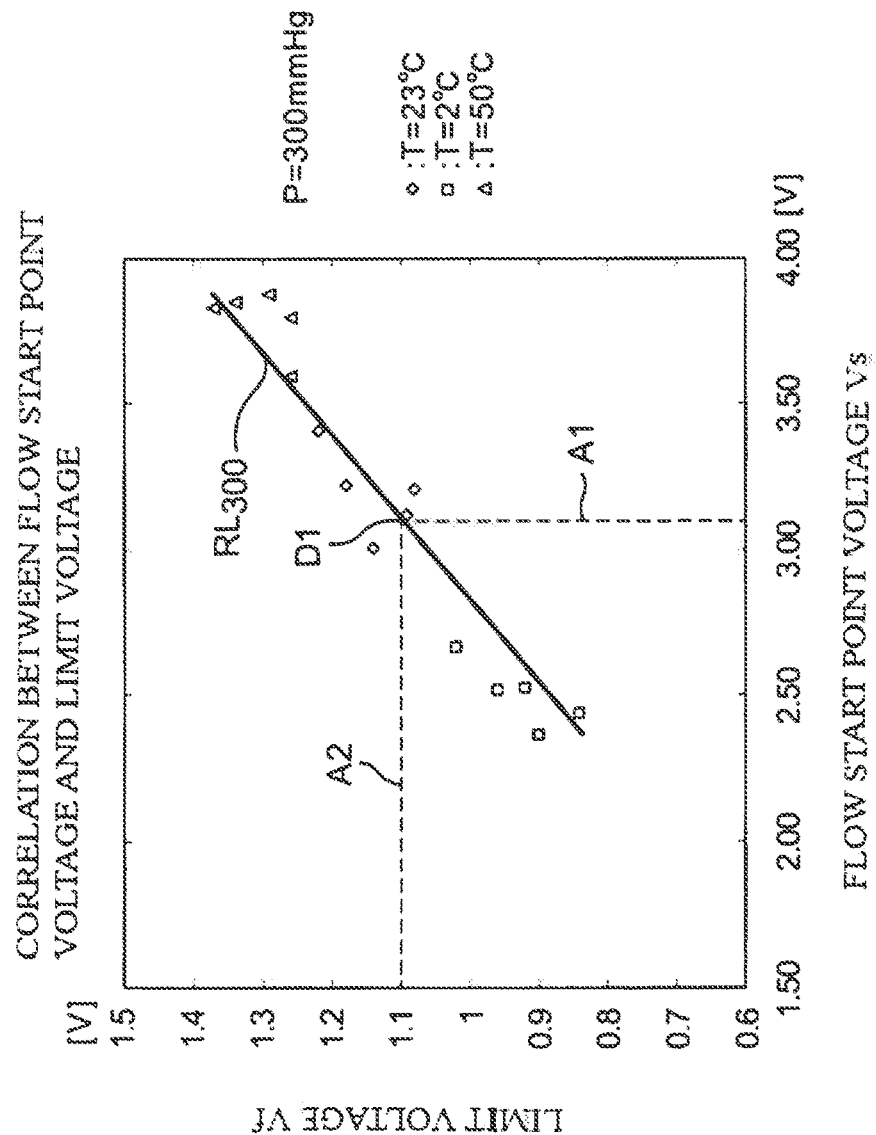
FIG. 8 is a diagram showing a correlation between a flow start point voltage Vs and a limit voltage Vf under a condition in which an upstream-side pressure P is set to 300 mmHg for five sample solenoid valves having substantially the same characteristic as the solenoid valve that is to be controlled.
Figure 9:
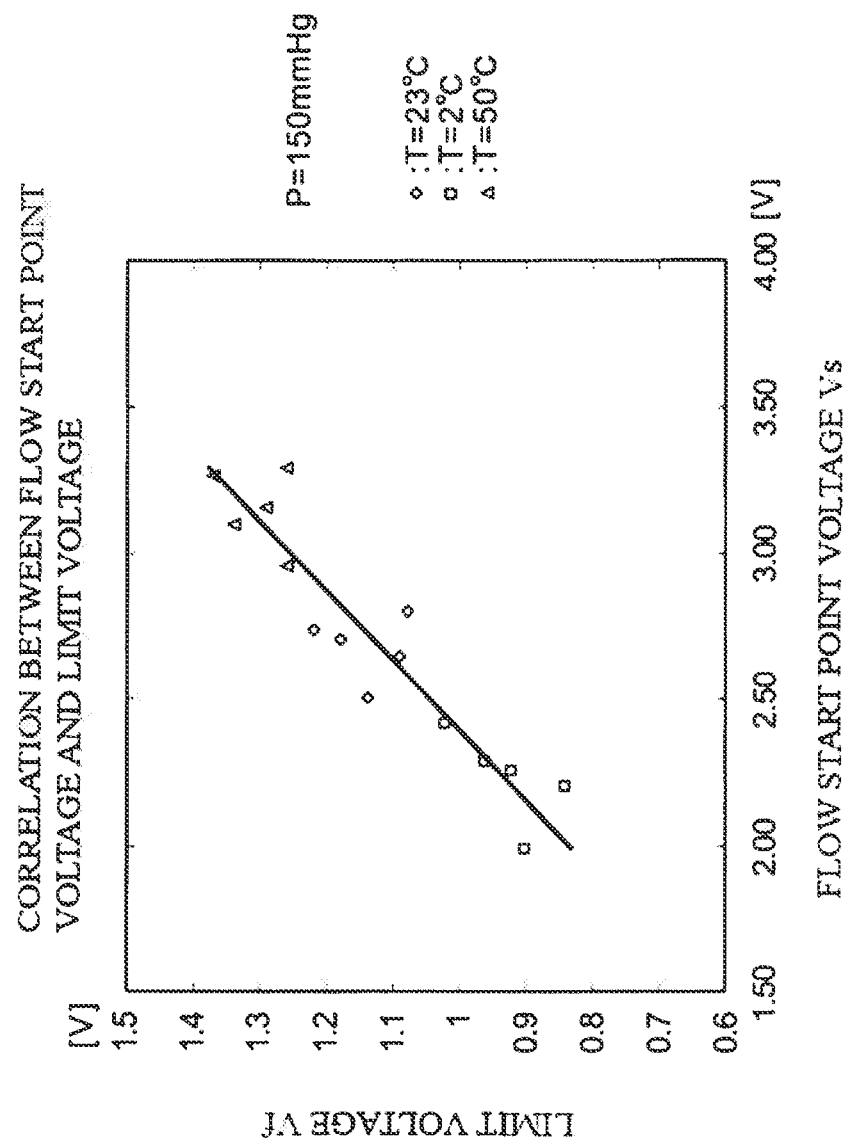
FIG. 9 is a diagram showing a correlation between a flow start point voltage Vs and a limit voltage Vf under a condition in which an upstream-side pressure P is set to 150 mmHg for five sample solenoid valves having substantially the same characteristic as the solenoid valve that is to be controlled.

FIGS. 8 and 9 show, as scatter diagrams, correlations between the flow start point voltage Vs and the limit voltage Vf under conditions in which the upstream-side pressures P of five sample solenoid valves having substantially the same Q-V characteristic (in this example, the same model number) as the solenoid valve 233 are set to 300 mmHg and 150 mmHg respectively. In these diagrams, each mark ◇ denotes a data point of one sample solenoid valve with a ambient temperature T of 23° C. (room temperature). Each mark □ denotes a data point of one sample solenoid valve with a ambient temperature T of 2° C. (low temperature). Also, each mark Δ denotes a data point of one sample solenoid valve with a ambient temperature T of 50° C. (high temperature).

As can be understood from FIG. 8, in the case where the pressure P on the upstream side is 300 mmHg, when multiple varied ambient temperatures T are set to 2° C., 23° C., and 50° C. as parameters, the flow start point voltages Vs and the limit voltages Vf for the five sample solenoid valves change, exhibiting a positive correlation. In this example, this correlation is approximated using a line segment $RL_{300}$ (hereinafter referred to as "correlation $RL_{300}$" as appropriate). Also, as can be understood from FIG. 9, in the case where the pressure P on the upstream side is 150 mmHg, when multiple varied ambient temperatures T are set to 2° C., 23° C., and 50° C. as parameters, the flow start point voltages Vs and the limit voltages Vf for the five sample solenoid valves change, exhibiting a positive correlation. In this example, this correlation is approximated using a line segment $RL_{150}$ (hereinafter referred to as "correlation $RL_{150}$" as appropriate).

Thus, in the case where the upstream-side pressure P is set to 300 mmHg and 150 mmHg, when the ambient temperature T changes, the flow start point voltage Vs and the limit voltage Vf exhibit the positive correlations $RL_{300}$ and $RL_{150}$. Accordingly, if the flow start point voltage Vs of the solenoid valve 233 is known, the limit voltage Vf of the solenoid valve 233 can be obtained through conversion using these correlations, regardless of the ambient temperature T. For example, in the case where the pressure P on the upstream side is 300 mmHg, if the flow start point voltage Vs of the solenoid valve 233 is 3.10V as indicated by broken line A1 in FIG. 8, the limit voltage Vf of the solenoid valve 233 can be determined as being about 1.10V, as indicated by broken line A2 in FIG. 8. In this case, the range (effective setting range) in which the driving voltage V for the solenoid valve 233 is to be set is from about 1.10V to 3.10V. Note that in FIG. 8, the point corresponding to Vs=3.10V and Vf=1.10V on the line segment $RL_{300}$ is indicated by reference sign D1.

As can be understood by comparing FIGS. 8 and 9, when the pressure P changes from 300 mmHg to 150 mmHg, the line segment $RL_{150}$ shifts to the left side relative to the line segment $RL_{300}$. It is conceivable that the reason for this is that the flow start point voltage Vs is more significantly influenced by the upstream-side pressure P than the limit voltage Vf is.

Figure 1:
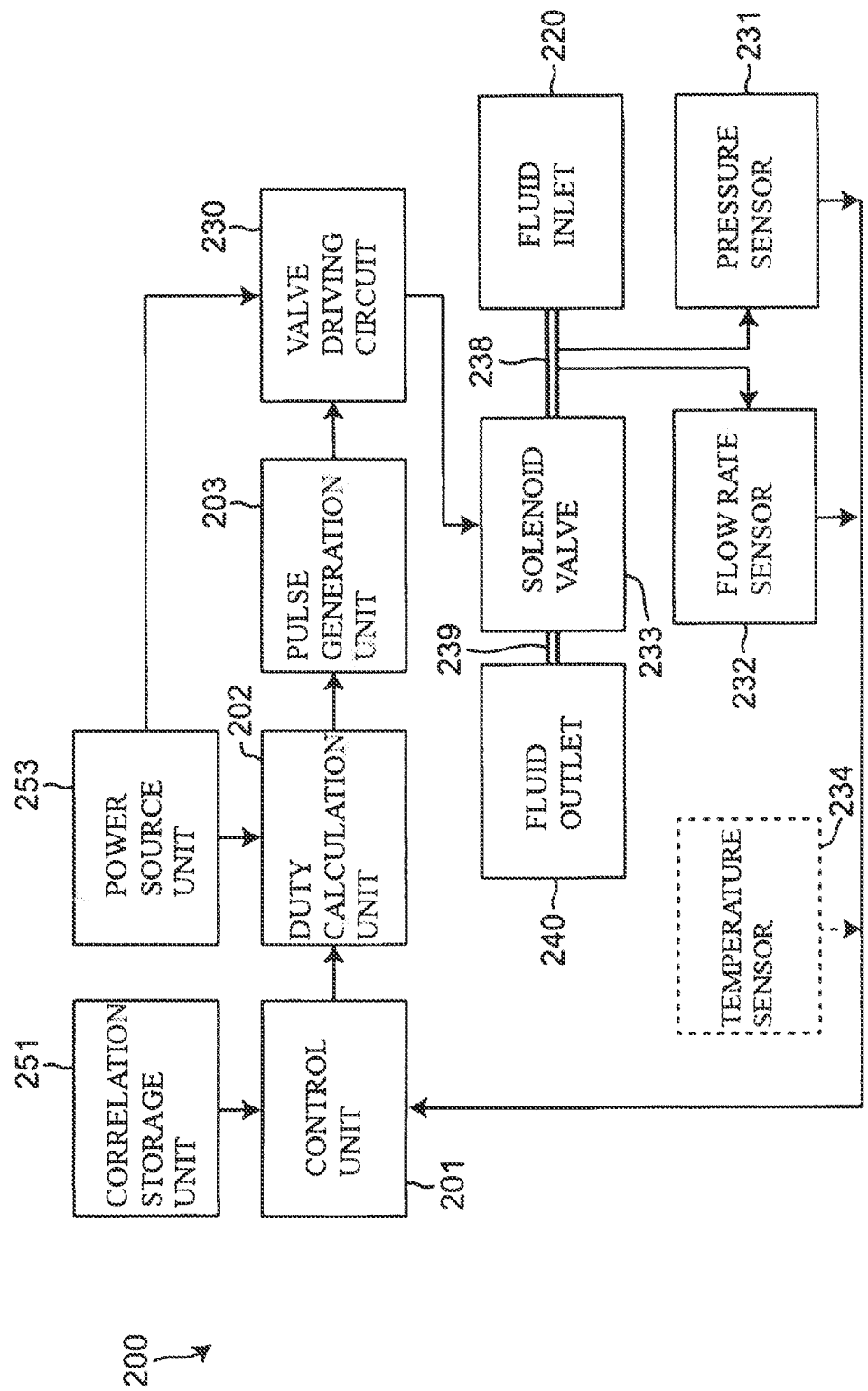
FIG. 1 is a diagram showing a block configuration of a flow rate control apparatus according to an embodiment of the invention.

FIG. 1 shows a block configuration of the flow rate control apparatus 200 according to an embodiment of the invention, which is based on the finding that there is a correlation between the flow start point voltage Vs and the limit voltage Vf of the solenoid valve 233. In order to control the flow rate of the fluid using the solenoid valve 233, the flow rate control apparatus 200 includes a correlation storage unit 251, a control unit 201, a duty calculation unit 202, a pulse generation unit 203, a valve driving circuit 230, a power source unit 253, a pressure sensor 231, and a flow rate sensor 232 serving as a flow rate detection unit.

The solenoid valve 233 is inserted between a pipe 238 connected to a fluid inlet 220 and a pipe 239 connected to a fluid outlet 240. The fluid is supplied from a pressure source (not shown) on the upstream side to the solenoid valve 233 (to the outer end 270*e* of the flow-through hole 270 of the solenoid valve 233) through the fluid inlet 220 and the pipe 238. The fluid that has passed through the solenoid valve 233 is emitted to the outer environment (at the atmospheric pressure) through the pipe 239 and the fluid outlet 240. Note that it is assumed that loss of pressure through the pipes 238 and 239 is negligible.

The pressure sensor 231 detects the pressure of the fluid passing through the pipe 238. A known piezoresistance-type pressure sensor, such as a commercially-available pressure sensor manufactured by Mitsumi Electric Co., Ltd. (e.g., product number MMR901XA, operation pressure range 0 to 40 kPa (300 mmHg)) or the like can be used as the pressure sensor 231.

A flow rate sensor 232 detects the flow rate of the fluid passing through the pipe 238. For example, a commercially-available MEMS (Micro Electro Mechanical Systems) flow sensor (model D6F-02A1-110, flow rate detection range 0 to 2 L/min) manufactured by Omron Corporation or the like can be used as the flow rate sensor 232.

Regarding the driving voltage of a sample solenoid valve having substantially the same characteristic as the solenoid valve 233 to be controlled, the correlation storage unit 251 stores the correlation between the flow start point voltage Vs at which the fluid starts to flow through the sample solenoid valve and the limit voltage Vf at which the sample solenoid valve is fully open. In this example, the formulae for the line segments $RL_{300}$ and $RL_{150}$, which express the correlations shown in FIGS. 8 and 9, are stored. In this example, the correlation storage unit 251 is composed as an EEPROM (Electrically Programmable Read Only Memory), but instead of this, the correlation storage unit 251 may be composed of a RAM (Random Access Memory), a memory card, an SSD (Solid State Drive), or the like.

The power source unit 253 supplies power to the units of the flow rate control apparatus 200. In particular, the power source unit 253 supplies a DC voltage (having a magnitude that corresponds to $V_0$ in FIG. 2A) to the duty calculation unit 202 and the valve driving circuit 230. In this example, it is assumed that the DC voltage $V_0$=6V.

The control unit 201 controls the overall operation of the flow rate control apparatus 200. In particular, based on the outputs of the pressure sensor 231 and the flow rate sensor 232, the control unit 201 calculates and determines a driving voltage V to be applied to the solenoid valve 233 (to the solenoid coil 279 of the solenoid valve 233) such that the flow rate Q of the fluid that passes through the solenoid valve 233 reaches a target flow rate ($Q_{TARGET}$). In this example, the control unit 201 is composed of a CPU (Central Processing Unit) and executes processing in accordance with a program and data stored in a memory (not shown).

The duty calculation unit 202 compares the driving voltage V determined by the control unit 201 and the DC voltage $V_0$ (=6V) supplied by the power source unit 253 and calculates a duty ratio (t1/t2) for creating the rectangular pulse waveform shown in FIG. 2A such that the driving voltage V determined by the control unit 201 is obtained with the valve drive circuit 230.

The pulse generation unit 203 generates a rectangular pulse waveform having the duty ratio (t1/t2) calculated by the duty calculation unit 202.

The functions of the duty calculation unit 202 and the pulse generation unit 203 are realized with the above-described processing of the CPU.

The valve driving circuit 230 includes a switching element (not shown) for switching the DC voltage $V_0$ (=6V) from the power source unit 253 on and off. The switching element is controlled so as to switch on and off using the rectangular pulse waveform from the pulse generation unit 203 (known PWM control). Accordingly, the valve driving circuit 230 outputs the rectangular pulse waveform shown in FIG. 2A as the driving voltage (effective value V) that is to be applied to the solenoid valve 233. The duty ratio of the pulse waveform to be output is (t1/t2) and the peak value is $V_0$=6V.

Figure 10:
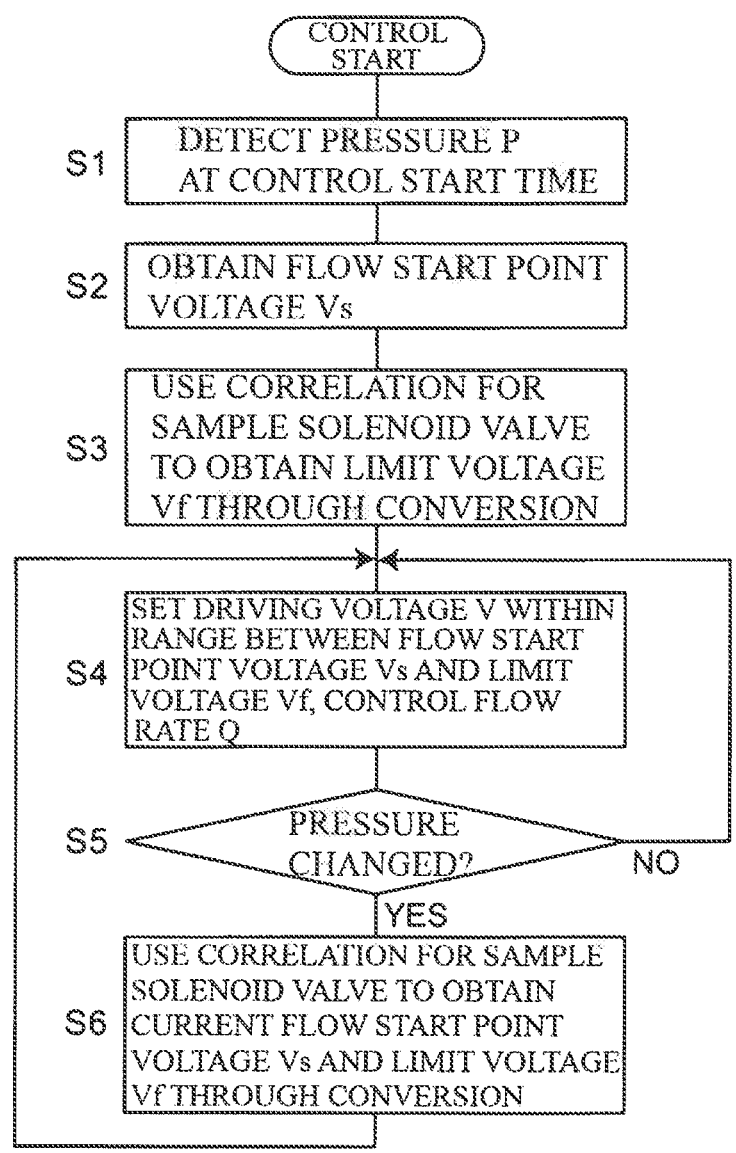
FIG. 10 is a diagram showing a flow of processing performed by a control unit of the flow rate control apparatus.

FIG. 10 shows a flow of processing performed by the control unit 201 of the flow rate control apparatus 200 to control the flow rate Q of the fluid using the solenoid valve 233. Note that this flow of processing is a flow for a relatively short period in which it is not necessary to consider changes in the ambient temperature T.

i) When the control is started, as shown in step S1 of FIG. 10, the control unit 201 first detects the current pressure (i.e., the pressure at the start of control) P of the fluid using the pressure sensor 231. In this example, the pressure at the start of control is P=300 mmHg.

ii) Next, the control unit 201 changes the driving voltage V of the solenoid valve 233, uses the flow rate sensor 232 to detect that the fluid has started to flow through the solenoid valve 233, and obtains the driving voltage for the time when the start of the flow of the fluid was detected as the flow start point voltage Vs (step S2 in FIG. 10). In this example, the flow start point voltage Vs is assumed to be 3.10V, as in the example indicated by the broken line A1 in FIG. 8. Note that the driving voltage V at this time is changed in the vicinity of the flow start point voltage Vs, from the high voltage side at which the solenoid valve 233 cuts off the fluid, to the flow start point voltage Vs. In other words, the driving voltage V is changed in a region that is sufficiently separated from the limit voltage Vf (in this example, from about 1.4 V to 0.8 V).

iii) Next, as shown in step S3 in FIG. 10, the control unit 201 uses the correlation (in this example, the equation of the line segment $RL_{300}$ that indicates the correlation shown in FIG. 8) for the sample solenoid valve stored in the correlation storage unit 251 according to the flow start point voltage Vs of the solenoid valve 233 to obtain the limit voltage Vf, at which the solenoid valve 233 is fully open, through conversion. In this example, due to the fact that the flow start point voltage Vs=3.10V, the limit voltage Vf of the solenoid valve 233 is obtained as 1.10V, as indicated by the broken line A2 in FIG. 8. As stated above, the limit voltage Vf can be obtained even if the ambient temperature T is not detected.

iv) Next, as shown in step S4 in FIG. 10, the control unit 201 controls the flow rate Q of the fluid with the driving voltage V of the solenoid valve 233 set within a range (effective setting range) between the flow start point voltage Vs and the limit voltage Vf. At this time, the flow rate Q of the fluid is controlled with the effective setting range set to 3.10V to 1.10V.

Specifically, the control unit 201 detects the current flow rate Q using the flow rate sensor 232 and obtains the difference (Q–$Q_{TARGET}$) between the current flow rate Q and the target flow rate $Q_{TARGET}$. Then, the control unit 201 calculates the driving voltage V that is to be applied to the solenoid valve 233 (to the solenoid coil 279 of the solenoid valve 233) such that the difference is zero. Here, if the driving voltage ($V_{CALC}$) calculated by the control unit 201 deviates from the effective setting range 3.10V to 1.10V, when $V_{CALC}$=1.05V for example, the control unit 201 corrects the driving voltage V to 1.15V, for example, in the vicinity of the limit voltage Vf in the effective setting range (0.05V being provided as a margin for the limit voltage Vf). The driving voltage V that is set by the control unit 201 in this manner in the effective setting range is applied to the solenoid valve 233 by the duty calculation unit 202, the pulse generation unit 203, and the valve driving circuit 230 in FIG. 1. Thus, feedback control is performed such that the flow rate Q of the fluid reaches the target flow rate $Q_{TARGET}$.

Thus, with the flow rate control apparatus 200, the correlation for the sample solenoid valves is used to obtain, through conversion, the limit voltage Vf at which the solenoid valve 233 is fully open, and therefore the driving voltage V of the solenoid valve 233 can be set accurately within the effective setting range.

v) Thereafter, as shown in step S5 of FIG. 10, as long as the pressure P detected by the pressure sensor 231 does not change (NO in step S5), the control of step S4 is continued at a constant period. The control unit 201 determines whether or not there is a change in pressure according to whether or not the difference (absolute value, i.e., |P–$P_{PREV}$|) between the pressure detected immediately beforehand (denoted as $P_{PREV}$) and the current pressure P has exceeded a threshold value (denoted as α; e.g., α=10 mmHg). Note that at the start of control, the current pressure P detected by the pressure sensor 231 is set as $P_{PREV}$.

vi) On the other hand, if the pressure P detected by the pressure sensor 231 changes (YES in step S5), or in other words, if |P–$P_{PREV}$|>α, the control unit 201 obtains, through conversion, the current flow start point voltage Vs and limit voltage Vf corresponding to the current pressure P for the solenoid valve 233, as shown in step S6 of FIG. 10.

Figure 11:
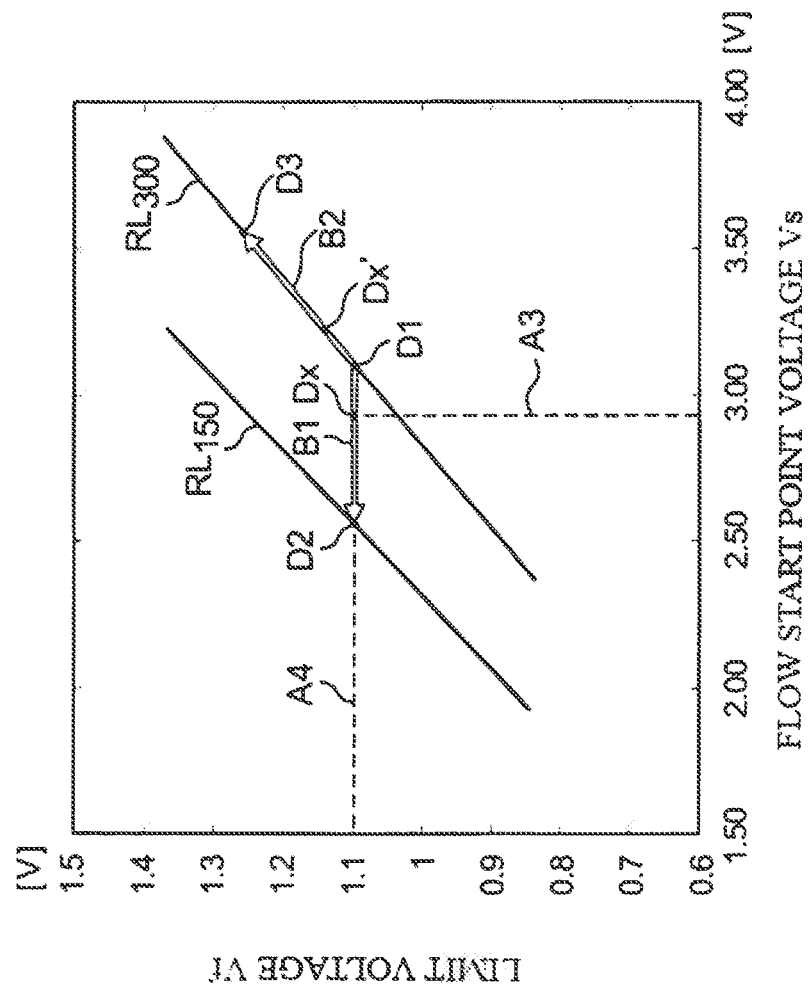
FIG. 11 is a diagram schematically showing a method of obtaining a current flow start point voltage Vs and limit voltage Vf through conversion in a case where the pressure of a fluid in the solenoid valve changes in a control period.

FIG. 11 schematically shows a method of obtaining, through conversion, the current flow start point voltage Vs and the limit voltage Vf in the case where the pressure P detected by the pressure sensor 231 has changed. FIG. 11 shows a point D1 corresponding to Vs=3.10V and Vf=1.10V at the control start time on the line segment $RL_{300}$ shown in FIG. 8 and a point D2 corresponding to the point D1 on a line segment $RL_{150}$ shown in FIG. 9. Also, the shifting of Vs and Vf from the point D1 to the point D2 when the pressure P changes from 300 mmHg to 150 mmHg is expressed as a vector B1.

Here, the current pressure P takes a value Px (in units of mmHg) between 300 mmHg and 150 mmHg that gives the correlation stored in the correlation storage unit 251, for example. At this time, the vector B1 (represents the shifting of Vs and Vf from the point D1 to the point D2) shown in FIG. 11 is multiplied by the ratio shown in the following equation (1):

$$(300 \text{ mmHg} - Px)/(300 \text{ mmHg} - 150 \text{ mmHg}) \quad (1)$$

and an internally dividing point Dx between the point D1 and the point D2 is obtained using interpolation. In the example shown in FIG. 11, the internally dividing point Dx indicates the flow start point voltage Vs=2.95V and the limit voltage Vf=1.10V (indicated by broken lines A3 and A4 in FIG. 11), which correspond to the current pressure P (=Px).

Thus, the current flow start point voltage Vs and the limit voltage Vf can be obtained through conversion in the case where the pressure P detected by the pressure sensor 231 has changed.

Note that when the current pressure P takes a value that exceeds 300 mmHg or is less than 150 mmHg, an externally dividing point (not shown) may be obtained using an interpolation method, and the flow start point voltage Vs and the limit voltage Vf indicated by the externally dividing point may be obtained. Alternatively, a correlation that covers such a pressure P may be stored in advance in the correlation storage unit 251 and obtained using interpolation.

vii) Next, the control unit 201 returns to step S4 of FIG. 10, and controls the flow rate Q of the fluid with the driving voltage V of the solenoid valve 233 set within a range (current effective setting range) between the flow start point voltage Vs (=2.95V) and the limit voltage Vf (=1.10V), which correspond to the current pressure P.

Thereafter, the control unit 201 repeats the processing of steps S6 and S4 each time the pressure P detected by the pressure sensor 231 changes (YES in step 55). Accordingly, even in the case where the pressure P of the fluid changes in the control period, the driving voltage V of the solenoid valve 233 can be set accurately in real time within the effective setting range.

Figure 12:
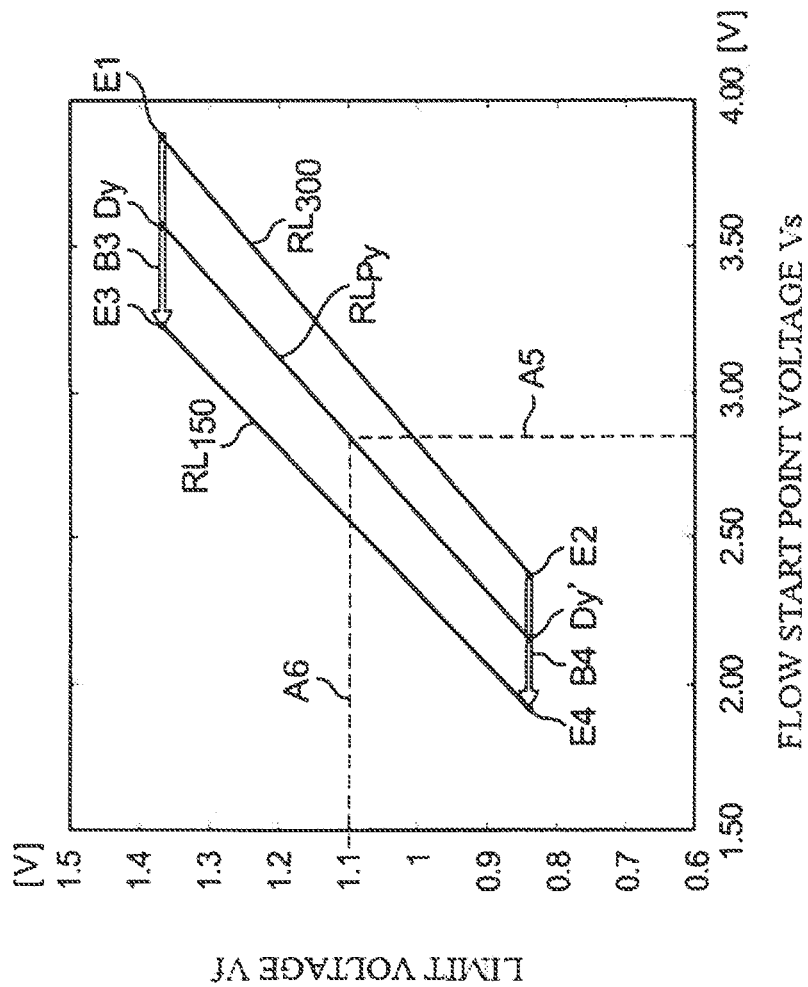
FIG. 12 is a diagram schematically showing a method of using interpolation to obtain a correlation between the flow start point voltage Vs and the limit voltage Vf, which correspond to the pressure of the fluid at a control start time, when the pressure at the control start time takes a value that is between the pressures 300 mmHg and 150 mmHg, which provide a correlation stored in a correlation storage unit.

In the example above, in step S1 of FIG. 10, the pressure at the control start time is P=300 mmHg, but there is no limitation to this. In the case where the pressure P at the control start time takes a value (denoted as Py) between 300 mmHg and 150 mmHg, for example, as shown in FIG. 12, the equations for the line segment $RE_{300}$ and the line segment $RL_{150}$ stored in the correlation storage unit 251 are used to obtain, through an interpolation method, an equation for a line segment $RL_{Py}$ indicating a correlation between the flow start point voltage Vs and the limit voltage Vf, which correspond to the pressure Py. For example, the shifting from the end points E1 and E2 of the line segment $RL_{300}$ to the end portion E3 and E4 corresponding to the line segment $RL_{150}$ is indicated by the vectors B3 and B4 respectively. The vectors B3 and B4 are multiplied by the following ratio (2):

$$(300 \text{ mmHg} - Py)/(300 \text{ mmHg} - 150 \text{ mmHg}) \quad (2)$$

and the internally dividing point Dy between the point E1 and the point E3 and the internally dividing point Dy' between the point E2 and the point E4 are obtained using an interpolation method. Then, the equation for the line segment connecting the internally dividing points Dy and Dy' is obtained as the equation for the line segment $RL_{Py}$ that indicates the correlation between the flow start point voltage Vs and the limit voltage Vf, which correspond to the pressure Py. Thereafter, in step S3 of FIG. 10, according to the flow start point voltage Vs of the solenoid valve 233, the line segment $RL_{Py}$ indicating the correlation is used to obtain, through conversion, the limit voltage Vf at which the solenoid valve 233 is fully open. For example, as indicated by the broken lines A5 and A6 in FIG. 12, if the flow start point voltage Vs of the solenoid valve 233 is 2.85V, the limit voltage Vf of the solenoid valve 233 can be obtained as 1.10V. Accordingly, even in the case where the pressure P at the control start time takes a value Py between 300 mmHg and 150 mmHg, for example, the driving voltage V of the solenoid valve 233 can be accurately set within a range (effective setting range) between the flow start point voltage Vs and the limit voltage Vf.

Note that when the pressure P at the control start time takes a value that exceeds 300 mmHg or is less than 150 mmHg, an interpolation method may be used to obtain the function for a line segment indicating the correlation between the flow start point voltage Vs and the limit voltage Vf corresponding to the pressure P. Alternatively, a correlation that covers such a pressure P may be stored in advance in the correlation storage unit 251 and obtained using interpolation.

Also, the above-described processing flow is a flow for a relatively short period in which there is no need to consider changes in the ambient temperature T, but there is no limitation to this.

For example, in FIG. 11, the shifting of Vs and Vf along the line segment $RL_{300}$ from the point D1 to the corresponding point D3 when the ambient temperature T changes from 23° C. (room temperature) to 50° C. (high temperature) under the condition that the pressure P=300 mmHg is indicated by the vector B2. A temperature sensor 234 (indicated by the dotted-line block in FIG. 1) is included so as to detect the difference (T−$T_{PREV}$) between a temperature detected immediately beforehand (denoted as $T_{PREV}$) and the current temperature T (in units of ° C.). The control unit 201 determines whether or not there is a change in the ambient temperature according to whether or not the difference (absolute value, i.e., |T−$T_{PREV}$|) has exceeded a threshold value (denoted as β; e.g., β=3° C). If the ambient temperature T detected by the temperature sensor changes, or in other words, if |T−$T_{PREV}$|>β, the current flow start point voltage Vs and the limit voltage Vf corresponding to the current ambient temperature T are obtained through conversion for the solenoid valve 233, Note that at the control start time, the current ambient temperature T detected by the temperature sensor 234 is set as $T_{PREV}$.

Specifically, the vector B2 (indicating the shifting of Vs and Vf from the point D1 to the point D3) shown in FIG. 11 is multiplied by the ratio in the following equation (3):

$$(T - 23° \text{ C.})/(50° \text{ C.} - 23° \text{ C.}) \quad (3)$$

and an internally dividing point Dx' between the point D1 and the point D3 is obtained using interpolation. The internally dividing point Dx' indicates the flow start point s voltage Vs and the limit voltage off corresponding to the current ambient temperature T (indicated by the broken lines A3 and A4 in FIG. 11).

Accordingly, even in the case where the ambient temperature T changes in the control period, the driving voltage V of the solenoid valve 233 can be set accurately in real time within the effective setting range.

Note that if the ambient temperature T drops from 23° C. (room temperature), data in which the ambient temperature T in FIG. 8 is 23° C. (room temperature) to 2° C. (low temperature) can be used. In this case, instead of equation (3), the ratio in the following equation (4):

$$(23° C.-T)/(23° C.-2° C.) \quad (4)$$

is used.

If both the pressure P and the ambient temperature T change, a vector obtained by compositing the vector B1 and the vector B2 can be used to obtain the flow start point voltage Vs and the limit voltage Vf corresponding to the current pressure P and ambient temperature T. Accordingly, even in the case where both the pressure P and the ambient temperature T change in the control period, the driving voltage V of the solenoid valve 233 can be set accurately in real time within the effective setting range.

In the example above, the solenoid valve 233 is of a normally-open type, but there is no limitation thereto. The flow rate control apparatus according to one or more embodiments of the invention can also be used to control a normally-closed type of solenoid valve. Also, regarding the "flow start point voltage Vs" and the "limit voltage Vf", depending on the type of the solenoid valve, there are cases where the flow start point voltage Vs is higher than the limit voltage Vf and there are cases where the flow start point voltage Vs is lower than the limit voltage Vf. The flow rate control apparatus according to one or more embodiments of the invention can be used in both cases.

Figure 13:
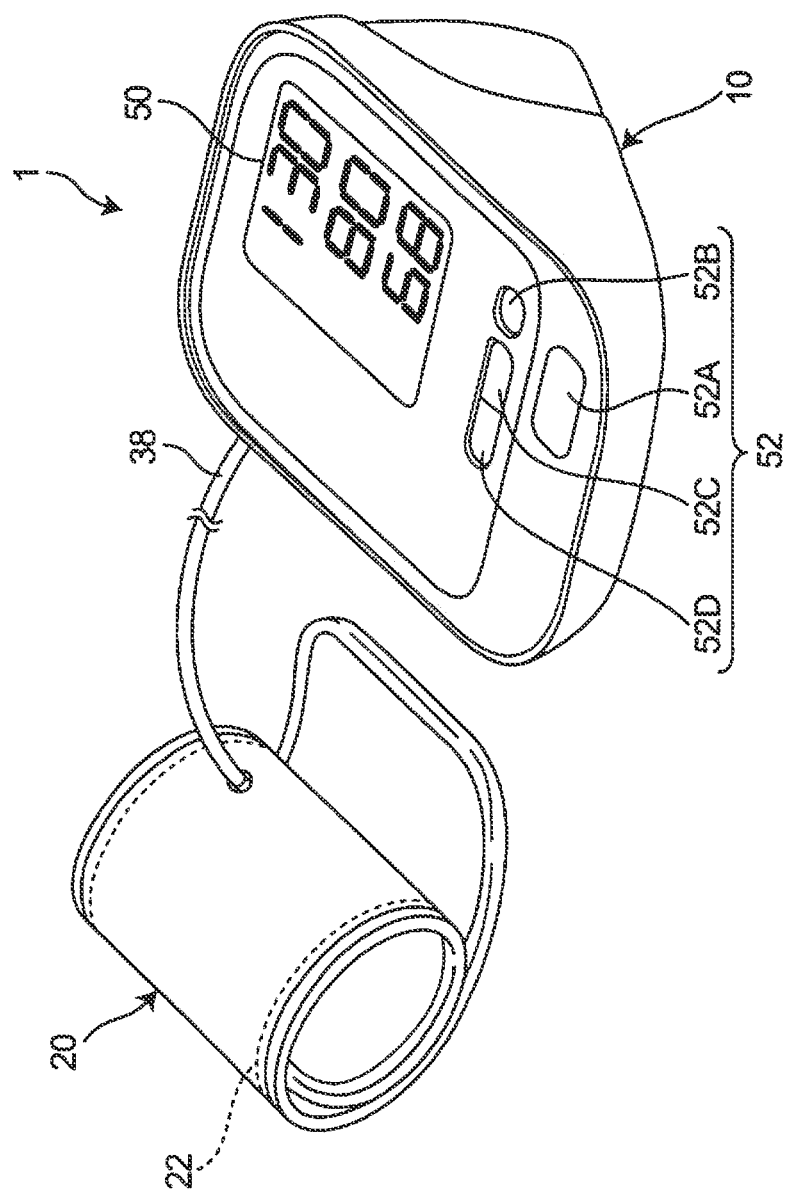
FIG. 13 is a diagram showing an exterior of an electronic blood pressure monitor according to an embodiment of the invention.

FIG. 13 shows the exterior of an electronic blood pressure monitor (indicated overall by reference numeral 1) according to an embodiment of the invention. The electronic blood pressure monitor 1 includes a cuff 20 worn on an upper arm of a measurement subject, a main body 10, and a flexible tube 38 that connects the cuff 20 and the main body 10. The cuff 20 contains a fluid bladder 22 for compressing the upper arm. The main body 10 is provided with a display device 50 and an operation unit 52. In this example, the operation unit 52 includes a power source switch 52A, a memory switch 52B, and forward/back switches 52C and 52D.

Figure 14:
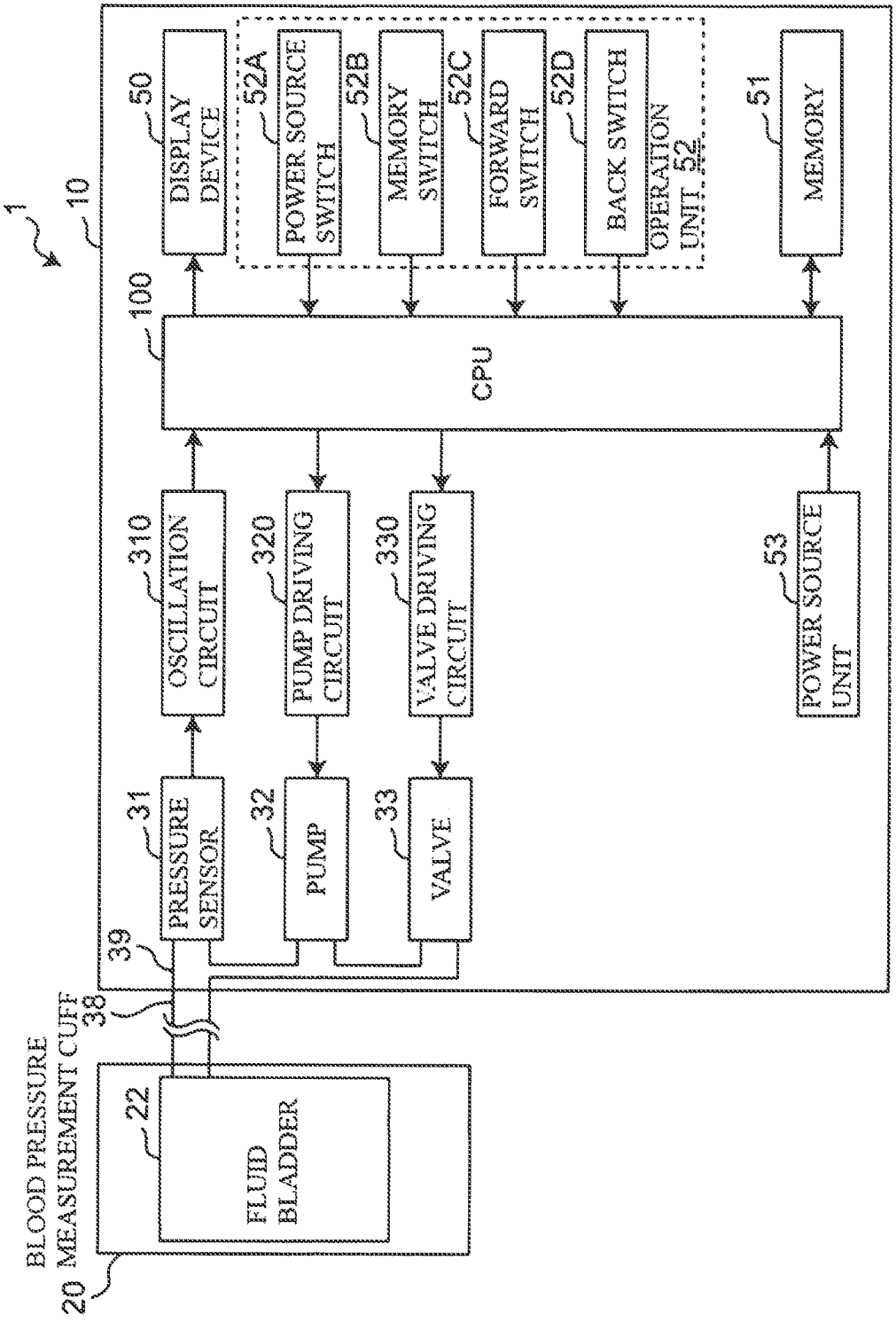
FIG. 14 is a diagram showing a schematic block configuration of the electronic blood pressure meter.

As shown in FIG. 14, in addition to the above-described display device 50 and the operation unit 52, a CPU (Central Processing Unit) 100, a memory 51, a power source unit 53, a piezoresistance-type pressure sensor 31, a pump 32 that supplies air serving as a fluid to the fluid bladder 22, a valve 33 (the same as the above-described solenoid valve 233) for adjusting the pressure (cuff pressure) of the fluid bladder 22, an oscillation circuit 310 that converts the output from the pressure sensor 31 into a frequency, a pump driving circuit 320 that drives the pump 32, and a valve driving circuit 330 (corresponds to the valve driving circuit 230 in FIG. 1) that drives the valve 33 are mounted in the main body 10. The pressure sensor 31, the pump 32, and the valve 33 are connected to the fluid bladder 22 contained in the cuff 20 via an air tube 39 provided in the main body interior, and the tube 38, which is in communication with the air tube 39. Accordingly, the air serving as the fluid flows between the pressure sensor 31, pump 32, and valve 33, and the fluid bladder 22.

The display device 50 includes a display, an indicator, and the like, and displays predetermined information in accordance with a control signal from the CPU 100.

With the operation unit 52, the power source switch 52A receives an instruction to switch the power source unit 53 on/off and an instruction to start blood pressure measurement. The memory switch 52B receives an instruction to display data on the measurement results of blood pressure values stored in the memory 51 on the is display device 50. The forward/back switches 52C and 52D receive changing instructions for causing the display device 50 to show display content from the past, or to advance the display content. The switches 52A, 52B, 52C, and 52D input operation signals corresponding to instructions given by the user to the CPU 100.

The memory 51 stores programs for controlling the electronic blood pressure monitor 1, setting data for setting various functions of the electronic blood pressure monitor 1, and data on the measurement results of the blood pressure value. Also, regarding the driving voltage of a sample solenoid valve having substantially the same characteristic as the valve 33 that is to be controlled, the memory 51 serves as the correlation storage unit to store the correlation between the flow start point voltage Vs at which the fluid starts to flow through the sample solenoid valve and the limit voltage Vf at which the sample solenoid valve is fully open. Also, the memory 51 is used as a work memory or the like for when a program is executed.

The power source unit 53 supplies power to the units, namely the CPU 100, the pressure sensor 31, the pump 32, the valve 33, the display device 50, the memory 51, the oscillation circuit 310, the pump driving circuit 320, and the valve driving circuit 330.

The oscillation circuit 310 oscillates based on an electrical signal value determined based on a change in electric resistance caused by a piezoresistant effect from the pressure sensor 31, and outputs a frequency signal having a frequency that corresponds to the electrical signal value of the pressure sensor 31 to the CPU 100.

Figure 15:
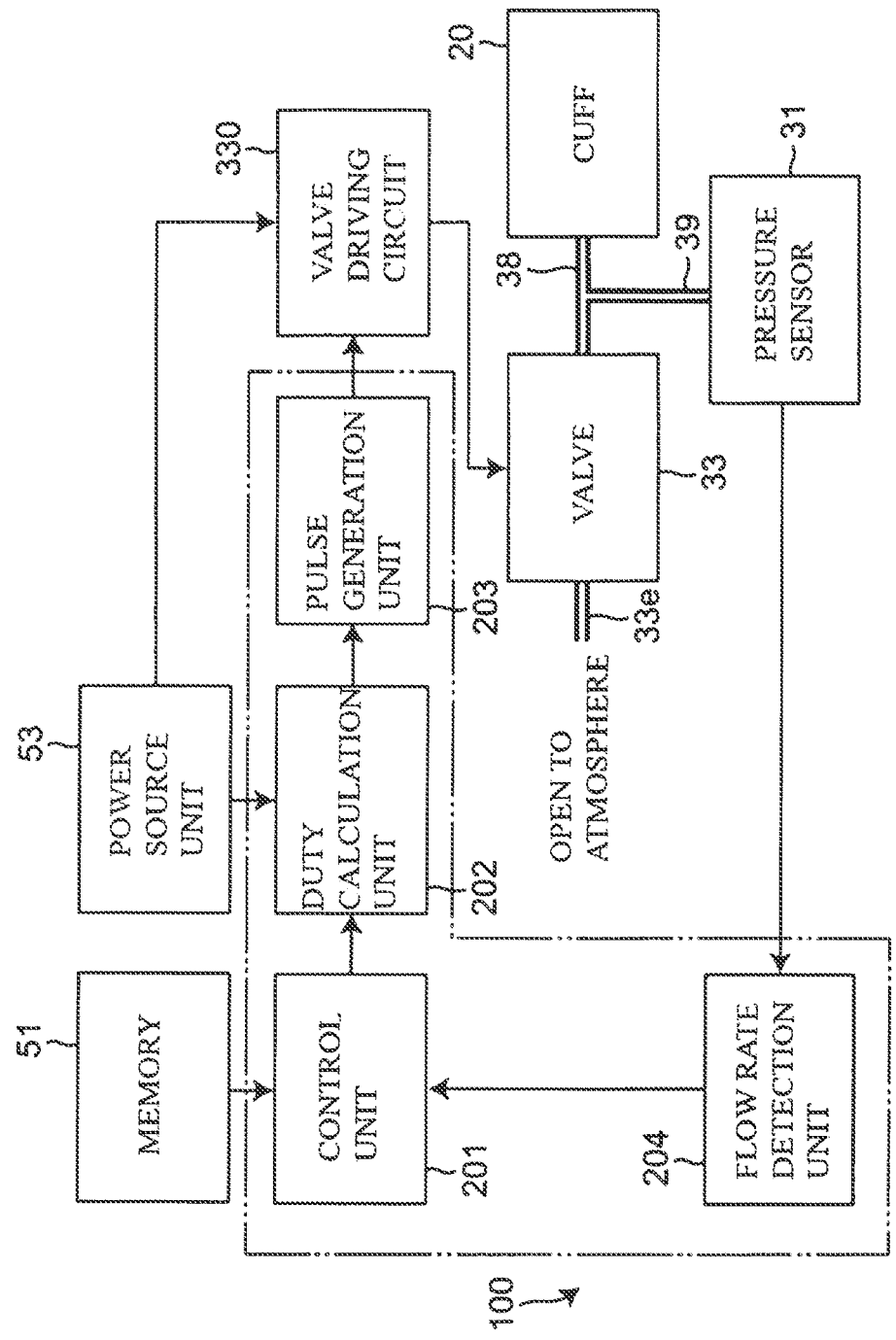
FIG. 15 is a diagram showing a block configuration of relevant portions relating to control of a solenoid valve of the electronic blood pressure meter.

In accordance with a program that is stored in the memory 51 and is for controlling the electronic blood pressure monitor 1, the CPU 100 performs control for driving the pump 32 via the pump driving circuit 320 and driving the valve 33 via the valve driving circuit 330 according to the operation signal from the operation unit 52. The valve 33 opens and closes in order to discharge or seal in the air in the fluid bladder 22 and thereby control the cuff pressure. Also, the CPU 100 calculates a blood pressure value based on the signal from the pressure sensor 31 and controls the display device 50 and the memory 51.

in particular, as shown in FIG. 15 (block configuration of relevant portions relating to the control of the solenoid valve), in order to adjust the flow rate of the air serving as the fluid using the valve 33, the CPU 100 functions as the above-described control unit 201, duty calculation unit 202, and pulse generation unit 203 (see FIG. 1) and functions as the flow rate detection unit 204. Note that as can be understood from FIG. 15, in this example, the temperature sensor is not provided.

The flow rate detection unit 204 calculates the flow rate Q (in units of ml/min) of the fluid that passes through the valve 33 based on the capacity of the fluid bladder 22 contained in the cuff 20 and on a change in the cuff pressure (pressure of the fluid bladder 22) detected by the pressure sensor 31.

Note that the air serving as the fluid passing through the valve 33 is emitted through the fluid outlet 33e of the valve 33 to the outside environment (in the atmosphere).

Figure 16:
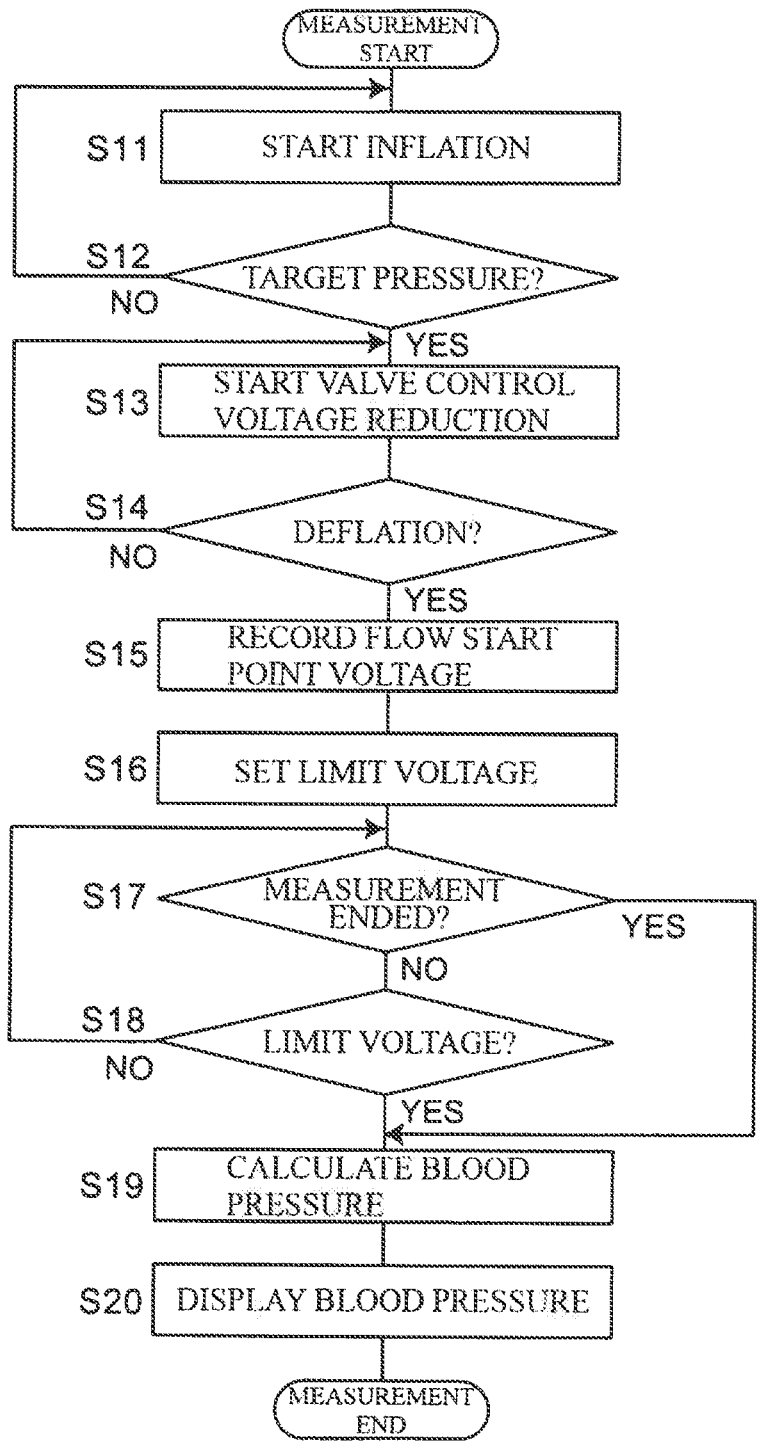
FIG. 16 is a diagram showing a flow of blood pressure measurement performed by the electronic blood pressure meter.

FIG. 16 shows a flow of blood pressure measurement performed by the electronic blood pressure monitor 1. The electronic blood pressure monitor 1 measures the blood pressure in accordance with a common oscillometric method.

Note that this measurement flow is a flow for a relatively short period in which it is not necessary to consider changes in the ambient temperature T. When measurement is to be performed, the cuff is wrapped around the measurement site (in this example, an upper arm) of the examination subject, and measurement start is instructed with an operation performed using the operation unit 52.

i) When blood pressure measurement is started, first, the CPU 100 closes the valve 33 via the valve driving circuit 330, and thereafter performs control for driving the pump 32 via the pump driving circuit 320, and sending air to the fluid bladder 22 while observing the cuff pressure P with the pressure sensor 31. Accordingly, the fluid bladder 22 is expanded and the cuff pressure gradually increases (step S11). When the cuff pressure is increased and the target pressure (set to be higher than the systolic blood pressure of the examination subject; in this example, 300 mmHg) is reached (YES in step S12), the CPU 100 stops the pump 32 via the pump driving circuit 320.

ii) Next, the CPU 100 gradually reduces the driving voltage V of the valve 33 via the valve driving circuit 330 (step S13), and detects that the air has started to flow through the solenoid valve 233 using the flow rate sensor 232 (YES in step S14). The driving voltage at the time of detecting the start of the flow of the air is obtained as the flow start point voltage Vs (step S15). Next, based on the flow start point voltage Vs, the correlation (in this example, the equation for the line segment $RL_{300}$ indicating the correlation shown in FIG. 8) for the sample solenoid valves stored in the memory 51 is used to obtain, through conversion, the limit voltage Vf at which the valve 33 is fully open. Then, the flow rate Q of the air is controlled with the driving voltage V of the valve 33 set within a range (effective setting range) between the flow start point voltage Vs and the limit voltage Vf (step 516). Because the equation for the line segment $RL_{300}$ stored in the memory 51 includes the relationship at the time when multiple ambient temperatures T are varied and set, the limit voltage Vf of the solenoid valve obtained by the CPU 100 corresponds to the ambient temperature T.

This makes it possible to accurately set the driving voltage V of the valve 33 in the vicinity of the limit voltage Vf in the effective setting range. Accordingly, the pressure can be reduced quickly by increasing the flow rate for discharging air at the deflation start time. As a result, the amount of time needed for blood pressure measurement can be shortened. Also, because the driving voltage V of the valve 33 does not fall below the limit voltage Vf, a situation can be avoided in which the cuff pressure suddenly drops during blood pressure measurement, causing a measurement error. Also, it is easier to use a low-cost solenoid valve that tends to have a smaller effective setting range.

iii) Next, the CPU 100 reduces the cuff pressure P at a target deflation speed that is suitable for blood pressure measurement, while observing the cuff pressure P using the pressure sensor 31. In the deflation process, the change in the cuff pressure P caused by the pulse wave at the measurement site is acquired (step S17).

iv) Thereafter, if the acquisition of the change in the cuff pressure P caused by the pulse wave ends (YES in step S17) or the air is completely discharged from the cuff 20 and the driving voltage V instructed by the CPU 100 reaches the limit voltage Vf (YES in step S18), the CPU 100 applies a known algorithm using the oscillometric method to the acquired data (change in the cuff pressure P caused by the pulse wave) and thereby calculates the blood pressure values (systolic blood pressure and diastolic blood pressure) (step S19). Hereinafter, the CPU 100 causes the calculated blood pressure values to be displayed on the display device 50 (step S20).

The blood pressure measurement is performed in about one minute, such that there is no need to consider a change in the ambient temperature T. Moreover, the limit voltage Vf of the solenoid valve obtained by the CPU 100 in step S16 described above corresponds to the ambient temperature T. Accordingly, even if no temperature sensor is included, the driving voltage V of the solenoid valve can be set accurately within the effective setting range.

Note that in the above-described deflation process, the CPU 100 may execute the processing (corresponds to step S6 in FIG. 10) for obtaining the correlation corresponding to the current cuff pressure P by interpolation, in real time. In such a case, the flow start point voltages Vs and the limit voltages Vf corresponding to the cuff pressures at those times can be obtained in real time through conversion. Accordingly, the driving voltage V of the valve 33 can be set accurately in real time within a range (effective setting range) between the flow start point voltage Vs and the limit voltage Vf.

Also, in an application where measurement is performed continuously for a long time, such as in the case of performing 24-hour blood pressure measurement, there is a possibility that both the pressure P and the ambient temperature T will change in the control period. In such a case, it is preferable that a temperature sensor is furthermore included and the ambient temperature T of the valve 33 is measured. Accordingly, by performing conversion using a vector obtained by compositing the vector B1 and the vector B2 shown in FIG. 11, the flow start point voltage Vs and the limit voltage Vf corresponding to the current pressure P and ambient temperature T can be obtained. Accordingly, even in the case where both the pressure P and the ambient temperature T change in the control period, the driving voltage V of the solenoid valve 33 can be set accurately in real time within the effective setting range.

The above-described embodiment is merely an example, and various modifications can be made without departing from the gist of the invention. The multiple above-described embodiments can be used individually, or in combination with each other Also, the various characteristics in the different embodiments can be used individually or in combination with each other.

REFERENCE SIGNS LIST

1 Electronic blood pressure monitor
20 Cuff
22 Fluid bladder
33 Valve
51 Memory
100 CPU
200 Flow rate control apparatus
201 Control unit
233 Solenoid valve
251 Correlation storage unit

The invention claimed is:

1. A flow rate control apparatus for controlling a flow rate of a fluid by opening and closing a solenoid valve using a driving voltage, comprising:
   a flow rate detection unit configured to detect the flow rate of the fluid flowing through the solenoid valve;
   a correlation storage unit storing, for a sample solenoid valve which is a different valve from the solenoid valve and has substantially the same characteristic as the solenoid valve, a correlation between a flow start point voltage of the sample solenoid valve at which the fluid starts to flow through the sample solenoid valve and a limit voltage of the sample solenoid valve at which the sample solenoid valve is fully open; and a control unit configured to, when starting control of the flow rate of the fluid, change the driving voltage of the solenoid valve, obtain the driving voltage at a time when the flow rate detection unit detects a start of flowing of the fluid as the flow start point voltage, use the correlation for the sample solenoid valve based on the flow start point voltage of the solenoid valve to obtain a limit voltage of the solenoid valve at which the solenoid valve is fully open through conversion, and thereafter set the driving voltage of the solenoid valve within a range between the flow start point voltage of the solenoid valve and the limit voltage of the solenoid valve.

2. The flow rate control apparatus according to claim 1, wherein
the correlation for the sample solenoid valve stored by the correlation storage unit includes the correlation at a time when a plurality of pressures of the fluid are set.

3. The flow rate control apparatus according to claim 2, comprising:
a pressure sensor configured to detect a pressure of the fluid,
wherein the control unit detects the pressure of the fluid at a control start time using the pressure sensor at the control start time,
when the pressure of the fluid at the control start time takes a value other than those of the plurality of pressures that give the correlation stored in the correlation storage unit, the control unit uses interpolation or extrapolation based on the correlation corresponding to the plurality of pressures to obtain a correlation between the flow start point voltage of the solenoid valve and the limit voltage of the solenoid valve corresponding to the pressure of the fluid at the control start time, and
the control unit uses the obtained correlation when obtaining the limit voltage of the solenoid valve through conversion based on the flow start point voltage of the solenoid valve.

4. The flow rate control apparatus according to claim 3, wherein
the control unit detects the pressure of the fluid after the control start time using the pressure sensor in a control period, and
when the pressure of the fluid after the control start time changes from the pressure of the fluid at the control start time, based on the correlation corresponding to the plurality of pressures, the control unit obtains the flow start point voltage of the solenoid valve and the limit voltage of the solenoid valve through conversion.

5. The flow rate control apparatus according to claim 4, wherein the correlation for the sample solenoid valve includes a relationship at a time when a plurality of varied ambient temperatures are set.

6. A blood pressure monitor comprising:
a cuff for compressing a measurement site;
a solenoid valve for adjusting a pressure of the cuff; and
the flow rate control apparatus according to claim 4.

7. The flow rate control apparatus according to claim 3, wherein the correlation for the sample solenoid valve includes a relationship at a time when a plurality of varied ambient temperatures are set.

8. A blood pressure monitor comprising:
a cuff for compressing a measurement site;
a solenoid valve for adjusting a pressure of the cuff; and
the flow rate control apparatus according to claim 3.

9. The flow rate control apparatus according to claim 2, wherein the correlation for the sample solenoid valve includes a relationship at a time when a plurality of varied ambient temperatures are set.

10. A blood pressure monitor comprising:
a cuff for compressing a measurement site;
a solenoid valve for adjusting a pressure of the cuff; and
the flow rate control apparatus according to claim 2.

11. The flow rate control apparatus according to claim 1, wherein the correlation for the sample solenoid valve includes a relationship at a time when a plurality of varied ambient temperatures are set.

12. The flow rate control apparatus according to claim 11, comprising:
a temperature sensor configured to detect an ambient temperature of the solenoid valve,
wherein the control unit detects the ambient temperature of the solenoid valve after a control start time using the temperature sensor in a control period, and
when the ambient temperature of the solenoid valve after the control start time changes from the ambient temperature at the control start time, based on the correlation corresponding to the plurality of ambient temperatures, the control unit obtains the flow start point voltage of the solenoid valve and the limit voltage of the solenoid valve through conversion.

13. A blood pressure monitor comprising:
a cuff for compressing a measurement site;
a solenoid valve for adjusting a pressure of the cuff; and
the flow rate control apparatus according to claim 12.

14. A blood pressure monitor comprising:
a cuff for compressing a measurement site;
a solenoid valve for adjusting a pressure of the cuff; and
the flow rate control apparatus according to claim 11.

15. A blood pressure monitor comprising:
a cuff for compressing a measurement site;
a solenoid valve for adjusting a pressure of the cuff; and
the flow rate control apparatus according to claim 1.

* * * * *